(12) United States Patent
Kundu et al.

(10) Patent No.: US 9,314,539 B2
(45) Date of Patent: Apr. 19, 2016

(54) NANOSPHERE-HISTONE ACETYLTRANSFERASE (HAT) ACTIVATOR COMPOSITION, PROCESS AND METHODS THEREOF

(71) Applicants: JAWAHARLAL NEHRU CENTRE FOR ADVANCED SCIENTIFIC RESEARCH, Bangalore, Karnataka (IN); UNIVERSITE DE STRASBOURG, Strasbourg (FR)

(72) Inventors: Tapas Kumar Kundu, Karnataka (IN); Anne-Laurence Boutillier, Strasbourg (FR); Snehajyoti Chatterjee, Karnataka (IN); Muthusamy Eswaramoorthy, Karnataka (IN); Pushpak Mizar, Karnataka (IN); Chantal Mathis, Strasbourg (FR); Jean-Christophe Cassel, Strasbourg (FR); Romain Neidl, Strasbourg (FR); Mohankrishna Dalvoy Vasudevarao, Karnataka (IN); Vedamurthy Bhusainahalli Maheshwarappa, Karnataka (IN)

(73) Assignees: JAWAHARLAL NEHRU CENTRE FOR ADVANCED SCIENTIFIC RESEARCH, Bangalore, Karnataka (IN); UNIVERSITE DE STRASBOURG, Strasbourg (FR)

( * ) Notice: Subject to any disclaimer, the term of this patent is extended or adjusted under 35 U.S.C. 154(b) by 0 days.

(21) Appl. No.: 14/397,561

(22) PCT Filed: Apr. 27, 2013

(86) PCT No.: PCT/IB2013/053343
§ 371 (c)(1),
(2) Date: Oct. 28, 2014

(87) PCT Pub. No.: WO2013/160885
PCT Pub. Date: Oct. 31, 2013

(65) Prior Publication Data
US 2015/0119466 A1    Apr. 30, 2015

(30) Foreign Application Priority Data

Apr. 28, 2012  (IN) .......................... 4646/CHE/2011

(51) Int. Cl.
| | |
|---|---|
| *A61K 31/167* | (2006.01) |
| *A61K 47/48* | (2006.01) |
| *C07K 14/47* | (2006.01) |
| *A61K 49/00* | (2006.01) |

(52) U.S. Cl.
CPC ......... *A61K 47/48861* (2013.01); *A61K 31/167* (2013.01); *A61K 47/48869* (2013.01); *A61K 49/0093* (2013.01); *C07K 14/47* (2013.01)

(58) Field of Classification Search
None
See application file for complete search history.

(56) References Cited

FOREIGN PATENT DOCUMENTS

| WO | 2004/053140 A2 | 6/2004 |
|---|---|---|
| WO | 2009/044410 A1 | 4/2009 |

OTHER PUBLICATIONS

Selvi et al. "Intrinsically Fluorescent Carbon Nanospheres as a Nuclear Targeting Vector: Delivery of Membrane-Impermeable Molecule to Modulate Gene Expression In Vivo," Nano Letters, vol. 8 No. 10, Oct. 8, 2008, pp. 3182-3188, with supporting information pp. 1-12.
Mantelingu et al., "Activation of p300 Histone Acetyltransferase by Small Molecules Altering Enzyme Structure: Probed by Surface-Enhanced Raman Spectroscopy," The Journal of Physical Chemistry B, vol. 111 No. 17, May 1, 2007, pp. 4527-4534.
Sep. 25, 2014 International Preliminary Report on Patentability issued in International Application No. PCT/IB2013/053343.
Aug. 21, 2013 Written Opinion issued in International Application No. PCT/IB2013/053343.
Aug. 21, 2013 International Search Report issued in International Application No. PCT/IB2013/053343.

*Primary Examiner* — Alicia L Otton
(74) *Attorney, Agent, or Firm* — Oliff PLC

(57) ABSTRACT

The present invention is in relation to a composition including nanosphere and histone acetyltransferase (HAT) activator. The nanosphere is carbon nanosphere (CSP) which is intrinsically fluorescent and the HAT activator is N-(4-Chloro-3-trifluoromethyl-phenyl)-2-n-propoxy-benzamide. The N-(4-Chloro-3-trifluoromethyl-phenyl)-2-n-propoxy-benzamide is covalently conjugated with the carbon nanosphere. The present invention further relates to a process for obtaining a composition including carbon nanosphere and Histone acetyltransferase (HAT) activator [N-(4-Chloro-3-trifluoromethyl-phenyl)-2-n-propoxy-benzamide]. The composition is capable of crossing blood brain barrier and inducing histone acetylation in brain. Further, the composition is capable of increasing neurogenesis, as well as improving long-term memory formation. The composition manages pathological conditions to a subject in need thereof, such as aging-related, neurodegenerative diseases (Alzheimer's in particular), neurological disorders, depression or other kinds of diseases in which increased HAT activity, neurogenesis and/or memory improvement would benefit.

14 Claims, 28 Drawing Sheets

A

B

Figure 27:
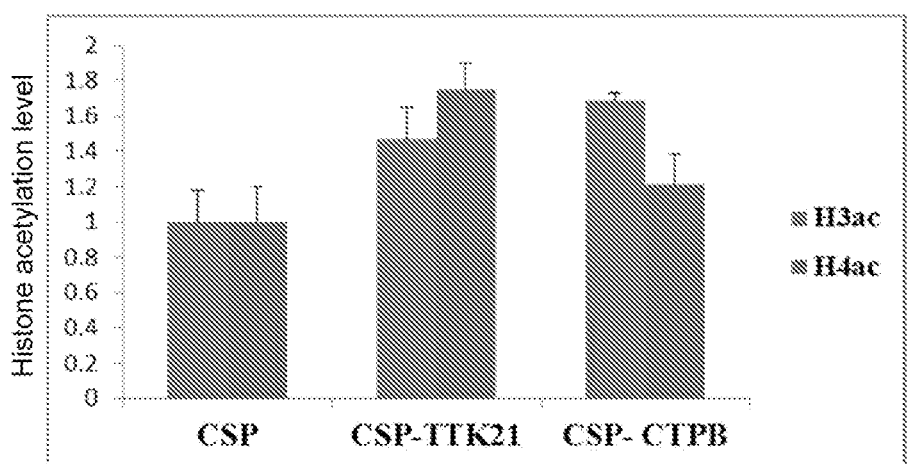

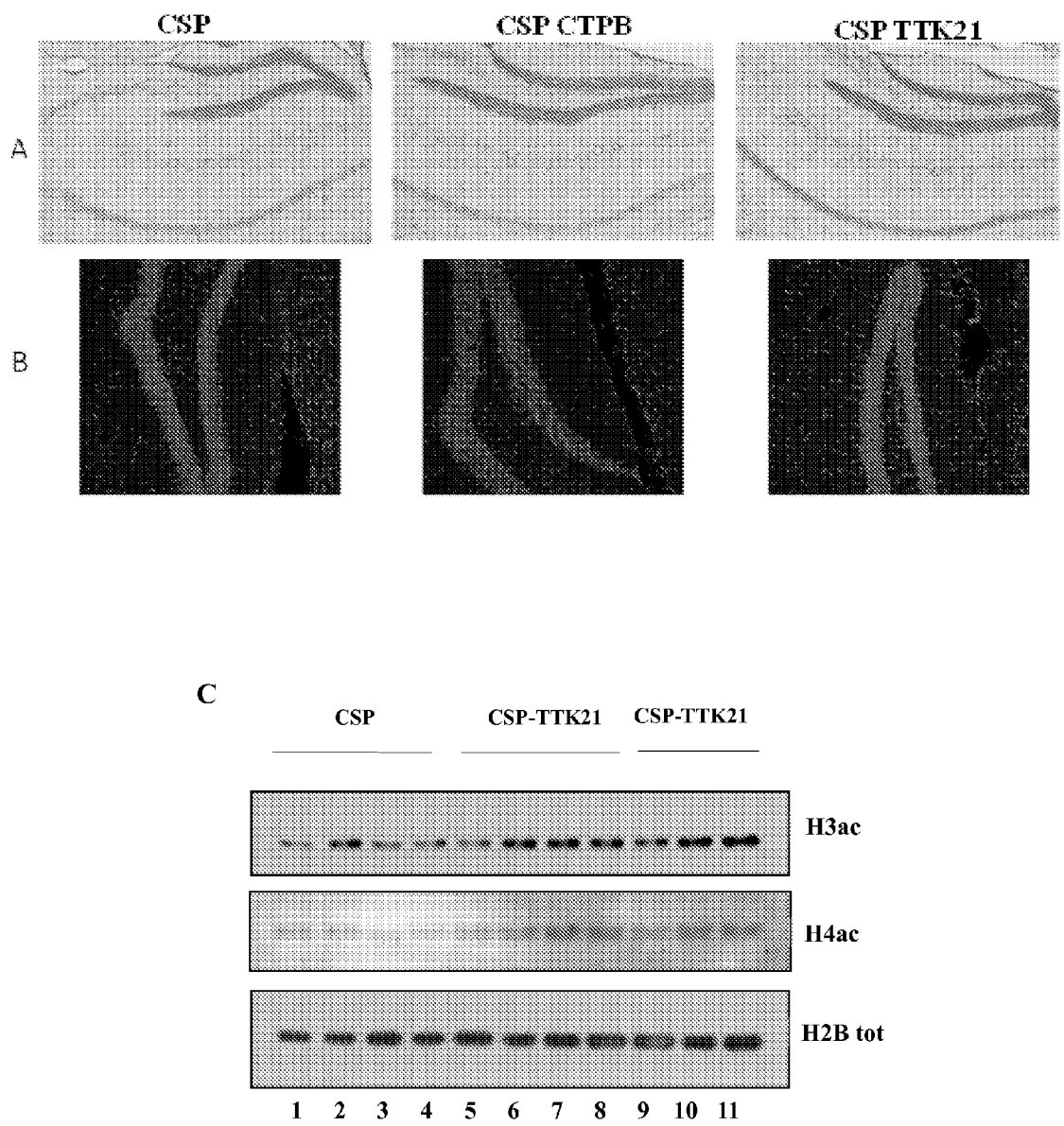
FIGURE 27 (A,B,C)

A

US 9,314,539 B2

NANOSPHERE-HISTONE ACETYLTRANSFERASE (HAT) ACTIVATOR COMPOSITION, PROCESS AND METHODS THEREOF

TECHNICAL FIELD

The present disclosure closure is in relation to a composition comprising nanosphere and Histone acetyltransferase (HAT) activator, process for obtaining the said composition and its implications in neurodegenerative disorders. In particular, the present disclosure aims at arriving at a composition comprising carbon nanosphere [CSP]-N-(4-Chloro-3-trinuoromethyl-phenyl)-2-n-propoxy-benzamide [COMPOUND 1 or TTK21] conjugate wherein, said conjugate is obtained by covalent conjugation of the COMPOUND 1 with the CSP. The composition is capable of inducing histone acetylation in organs such as brain, liver and spleen.

BACKGROUND OF THE DISCLOSURE

DNA is present in the nucleus of a cell in a very highly compacted state called chromatin. Chromatin is a combination of DNA, protein and RNA. The protein component of the chromatin is composed of histones and other non-histone proteins. The basic unit of a chromatin is nucleosome and is composed of dimers of histones H2A and H2B and tetramer of H3 and H4. The histones contain a highly dynamic N-terminal tails. The N terminal tails undergo various post translational modifications such as phosphorylation, acetylation, methylation, sumoylation, ubiquitinition and so on. Acetylation occurs on the lysine residues in the N-terminal tail where the acetyl group is transferred from acetyl CoA by the enzymatic activity of histone acetyltransferases (HATs). This acetylation is a reversible reaction, where the deacetylation is performed by another group of enzymes called the histone deaectylases (HDACs). The acetylation of the histone tails induces a more relaxed chromatin conformation enhancing the accessibility of the transcription machinery and resulting in transcription activation. On the contrary, histone deacetylation compacts the chromatin and induces transcription silencing.

Balance of histone acetylation gets altered in various diseases e.g., Cancer, AIDS and neurodegenerative diseases such as Alzheimer's or Huntington's diseases. In various neurodegenerative diseases like Alzheimer, several histone acetylation marks go down in the brain. Thus, small molecule activators of histone acetyltransferases could be potential drugs for neurodegenerative diseases. However, most of these small molecule HAT activators are unable to cross the blood brain barrier, and hence, the necessity for a delivering agent/carrier for delivering the small molecule HAT activators is immense.

Recently, nanotechnology has made lots of prospects in drug delivery. However, there are no reports showcasing efficient delivery of small molecule HAT activators.

Hence, the present disclosure aims at overcoming the aforesaid drawbacks of the prior art and providing for improved and efficient HAT activator compositions.

STATEMENT OF THE DISCLOSURE

Accordingly, the present disclosure relates to a composition comprising nanosphere and histone acetyltransferase (HAT) activator, wherein the HAT activator is N-(4-Chloro-3-trifluoromethyl-phenyl)-2-n-propoxy-benzamide; a process for obtaining a composition comprising nanosphere and histone acetyltransferase (HAT) activator, wherein the HAT activator is N-(4-Chloro-3-trifluoromethyl-phenyl)-2-n-propoxy-benzamide, said process comprising act of conjugating the N-(4-Chloro-3-trifluoromethyl-phenyl)-2-n-propoxy-benzamide with the nanosphere to obtain said composition; a method of inducing acetylation of histone by histone acetyltransferase (HAT), said method comprising act of contacting said histone acetyltransferase (HAT) with a composition comprising nanosphere and histone acetyltransferase (HAT) activator wherein the HAT activator is N-(4-Chloro-3-trifluoromethyl-phenyl)-2-n-propoxy-benzamide, for inducing the acetylation of histone; and a method of inducing neurogenesis or enhancing long-term memory formation or a combination thereof, said method comprising act of administering in a subject, a composition comprising nanosphere and histone acetyltransferase (HAT) activator wherein the HAT activator is N-(4-Chloro-3-trifluoromethyl-phenyl)-2-n-propoxy-benzamide.

BRIEF DESCRIPTION OF THE ACCOMPANYING FIGURES

Figure 1:
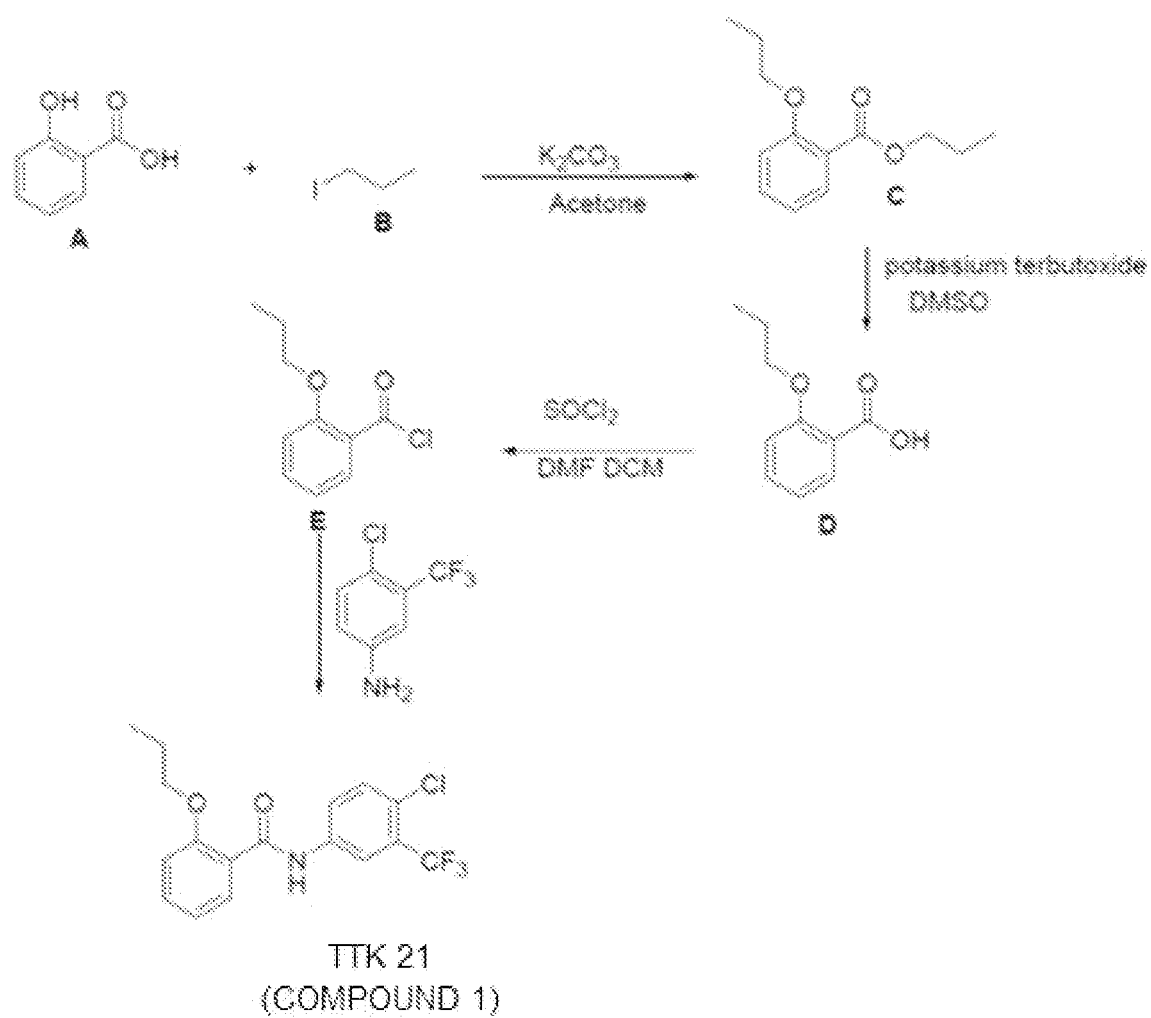

In order that the disclosure may be readily understood and put into practical effect, reference will now be made to exemplary embodiments as illustrated with reference to the accompanying figures. The figure together with a detailed description below, are incorporated in and form part of the specification, and serve to further illustrate the embodiments and explain various principles and advantages, in accordance with the present disclosure where:

FIG. 1 depicts the synthesis of N-(4-Chloro-3-trifluoromethyl-phenyl)-2-n-propoxy-benzamide TTK21 (COMPOUND 1).

Figure 2:
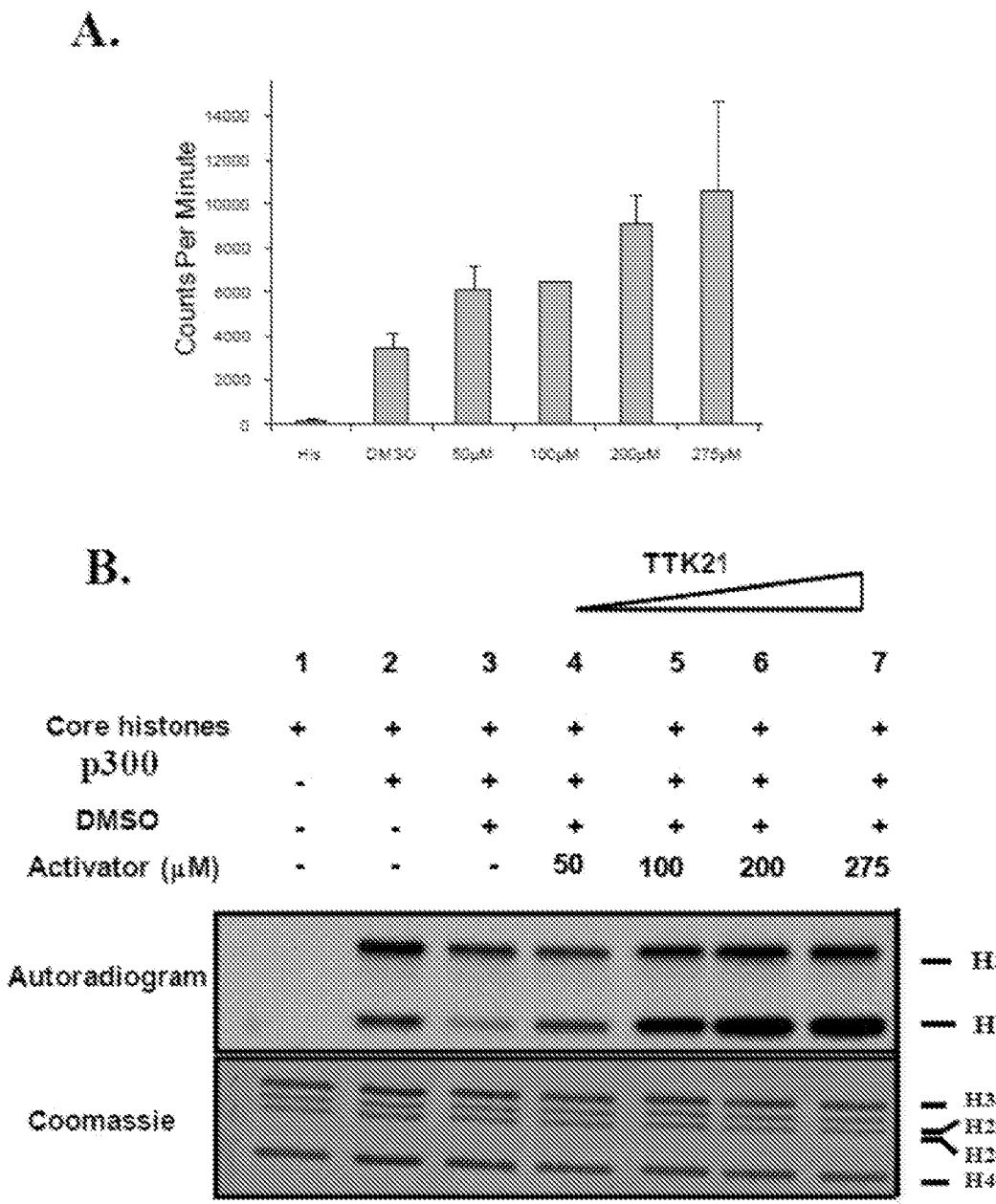

FIG. 2 depicts (A) filter binding assay to show activation of p300 by TTK21. Dose dependent activation of p300 by TTK21 as seen by Filter binding assay using TTK21 at 50 µM, 100 µM, 200 µM, and 275 µM; (B) gel fluorography assay to show dose dependent activation of p300 by TTK21. TTK21 dissolved in DMSO is added to the reaction mixture at desired concentrations. Lane 1—Histone only, Lane 2—p300 enzyme added, Lane 3—DMSO added, Lane 4—50 µM TTK21, Lane 5—100 µM TTK21, Lane 6—200 µM TTK21 and Lane 7—275 µM TTK21.

Figure 3:
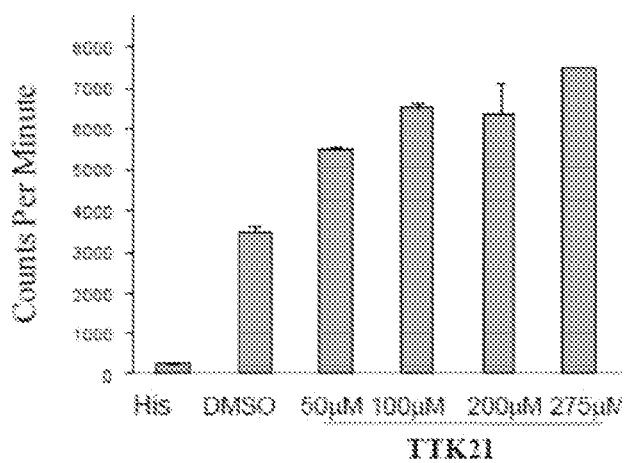
Figure 3:
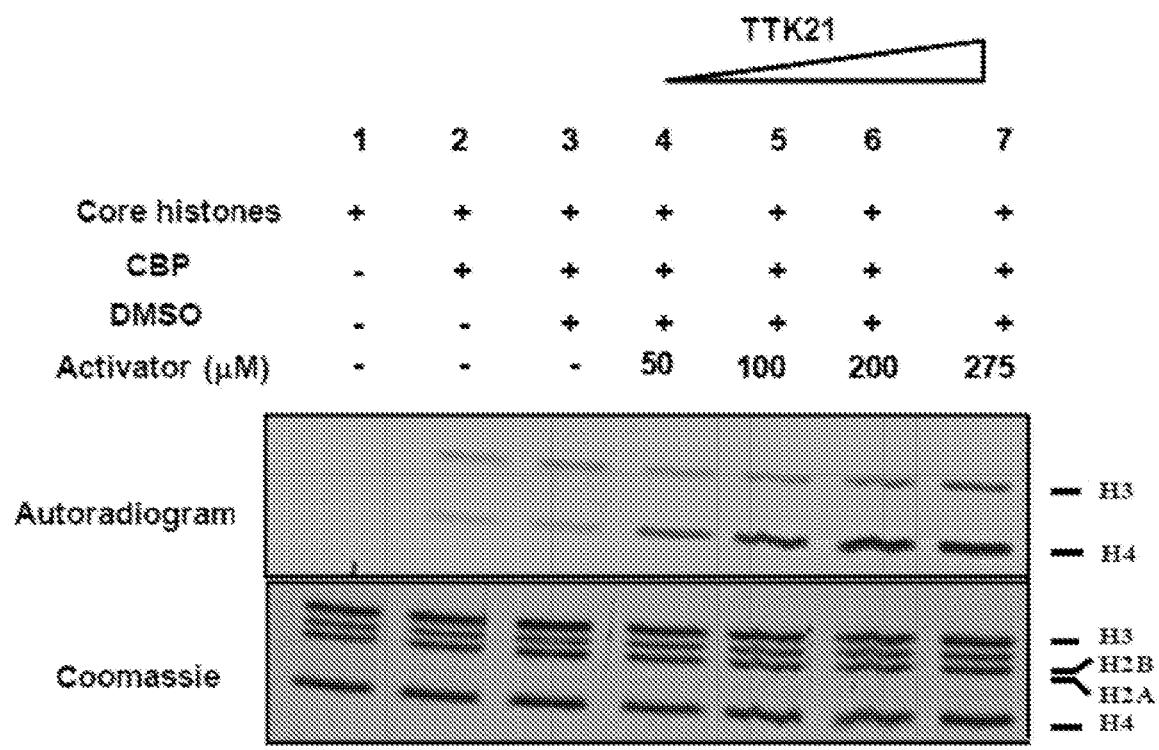

FIG. 3 depicts (A) dose dependent activation of CBP by TTK21 as seen by Filter binding assay using TTK21 at 50 µM, 100 µM, 200 µM, and 275 µM; (B) gel fluorography assay to show dose dependent activation of CBP by TTK21. TTK21 dissolved in DMSO is added to the reaction mixture at desired concentrations. Lane 1—Histone only, Lane 2—CBP enzyme added, Lane 3—DMSO added, Lane 4—50 µM TTK21, Lane 5—100 µM TTK21, Lane 6—200 µM TTK21 and Lane 7—275 µM TTK21.

Figure 4:
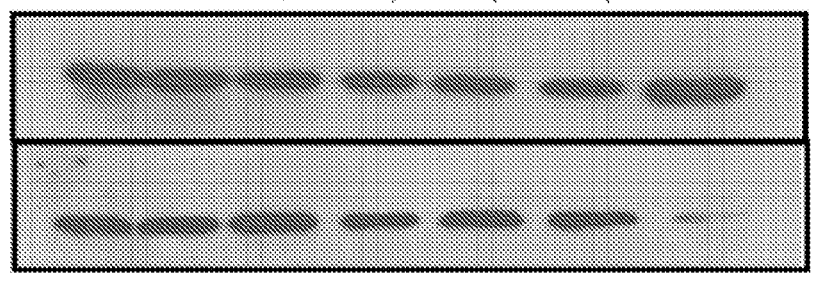

FIG. 4 depicts TTK21 being impermeable to cells. (A) western blot analysis of TTK21 untreated and treated HeLa cells for 24 hours. Lane 1—Untreated cells, Lane 2—DMSO treated cells, Lane 3—50 µM TTK21 treatment, Lane 4—100 µM TTK21, Lane 5—200 µM TTK21, Lane 6—275 µM TTK21 and Lane 7—500 µM Sodium butyrate (NaBu) treated cells. Primary probing of the blot is done with AcH3 and re-probing is done by H3 antibody.

Figure 5:
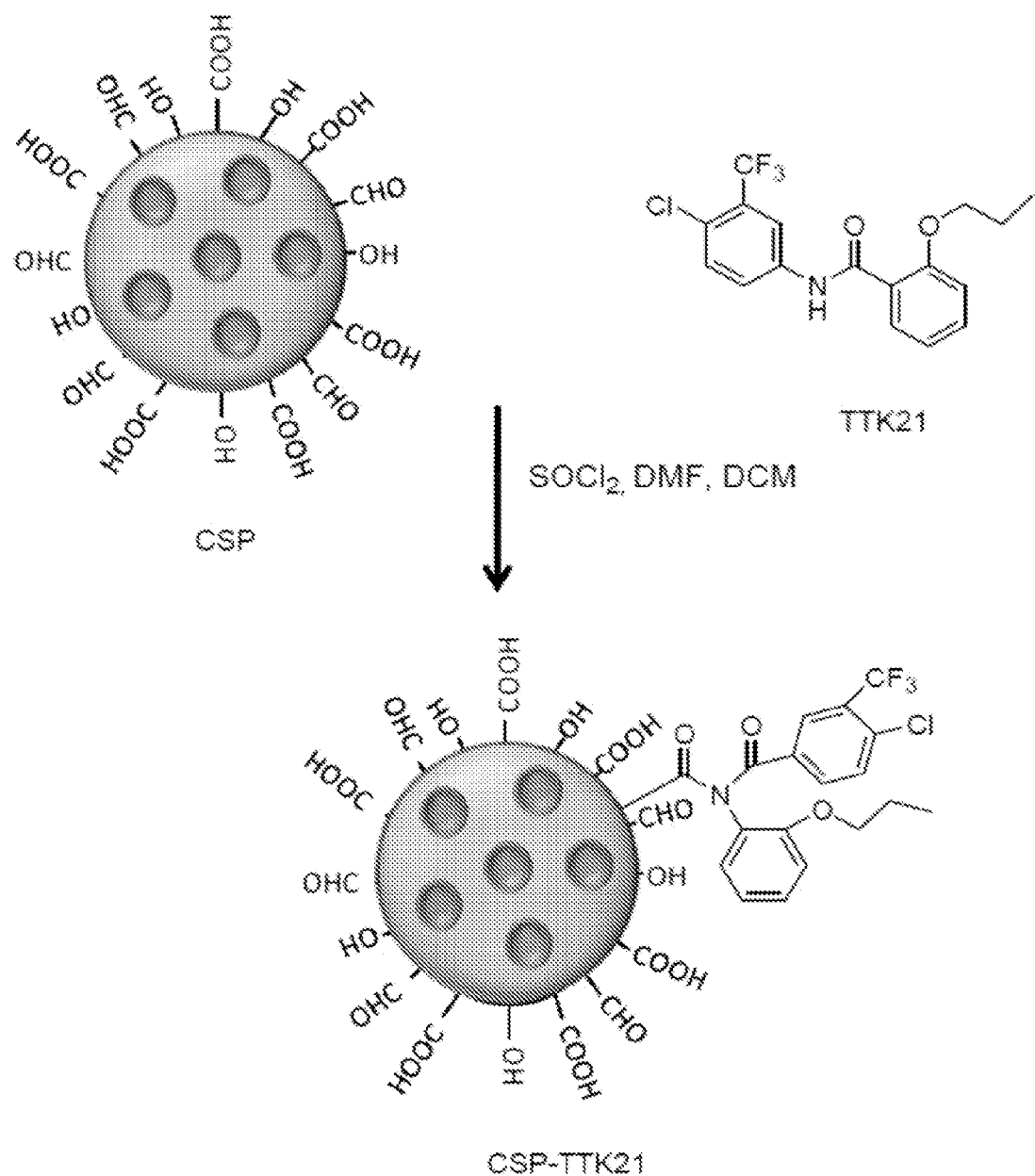

FIG. 5 depicts the synthesis of Carbon nanosphere conjugated TTK21 (CSP-TTK21).

Figure 6:
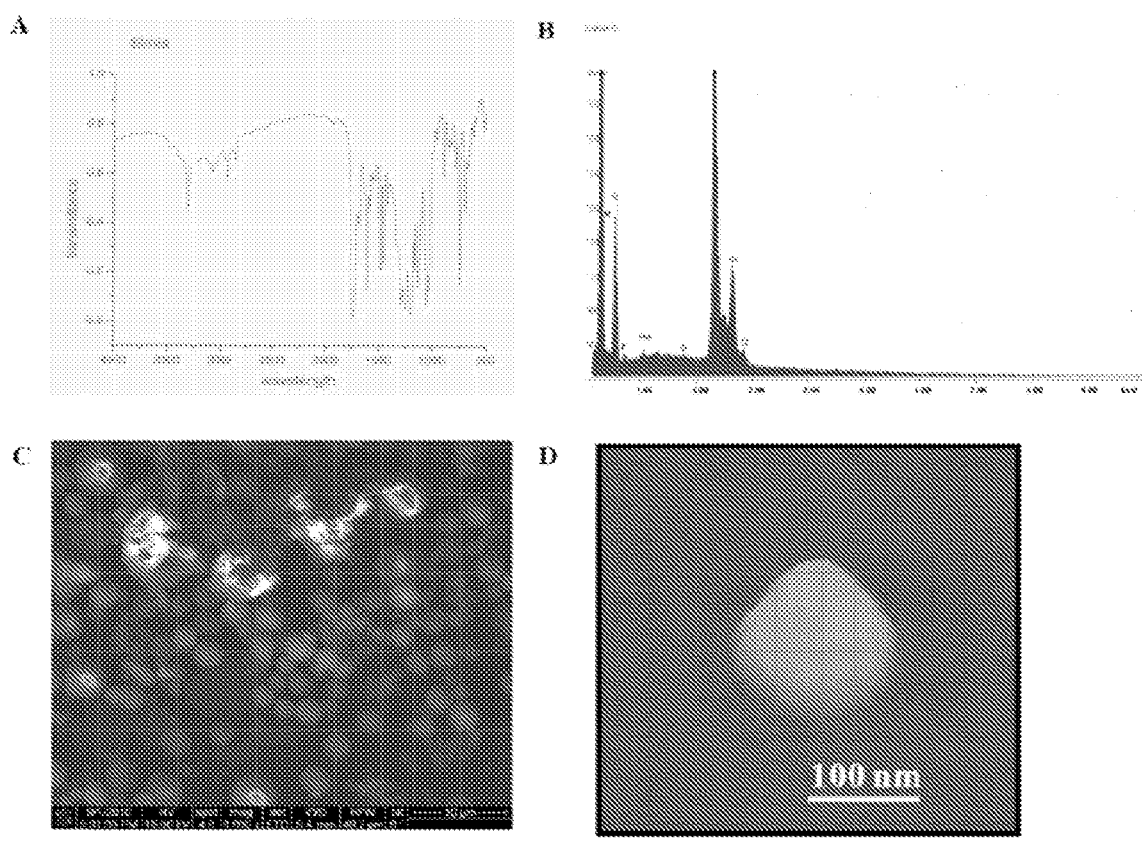

FIG. 6 depicts chemical characterization of TTK21 conjugated to Carbon nanospheres (CSP-TTK21); (A) IR (Infrared spectroscopy) analysis of CSP TTK21; (B) EDX (Energy-dispersive X-ray spectroscopy) analysis of CSP-TTK21: shows the presence of Fluorine, thereby confirming the conjugation of TTK21 with CSP; (C) SEM (Scanning electron microscope) image of CSP-TTK21 showing that the particles (i.e. CSP) still retain their spherical shape after conjugation; (D) AFM (Atomic Force Microscopy) image of CSP-TTK21.

Figure 7:
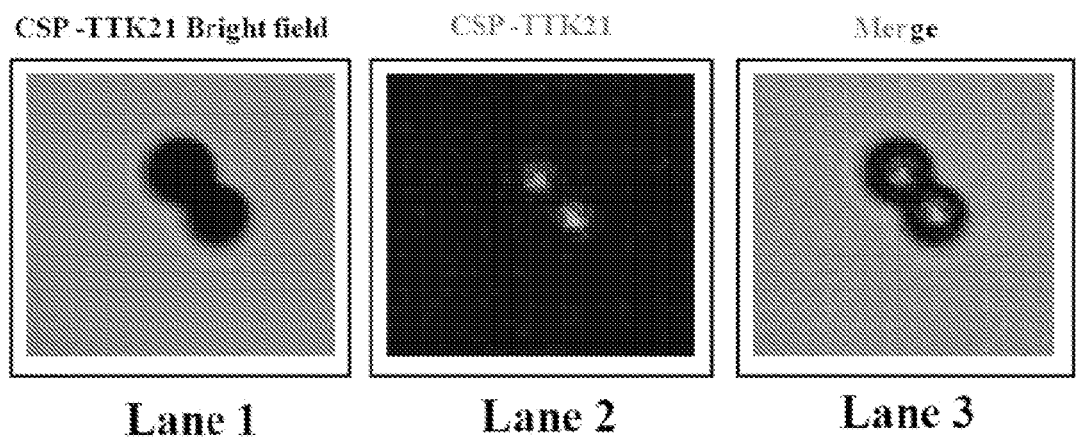

FIG. 7 depicts TTK21 conjugation to CSP as observed by fluorescence emission in vitro: Bright field image of Carbon nanosphere (CSP) [lane 1] and confocal laser scanning image of CSP upon excitation at 514 nm showing fluorescence at 560 nm (lane 2).

Figure 8:
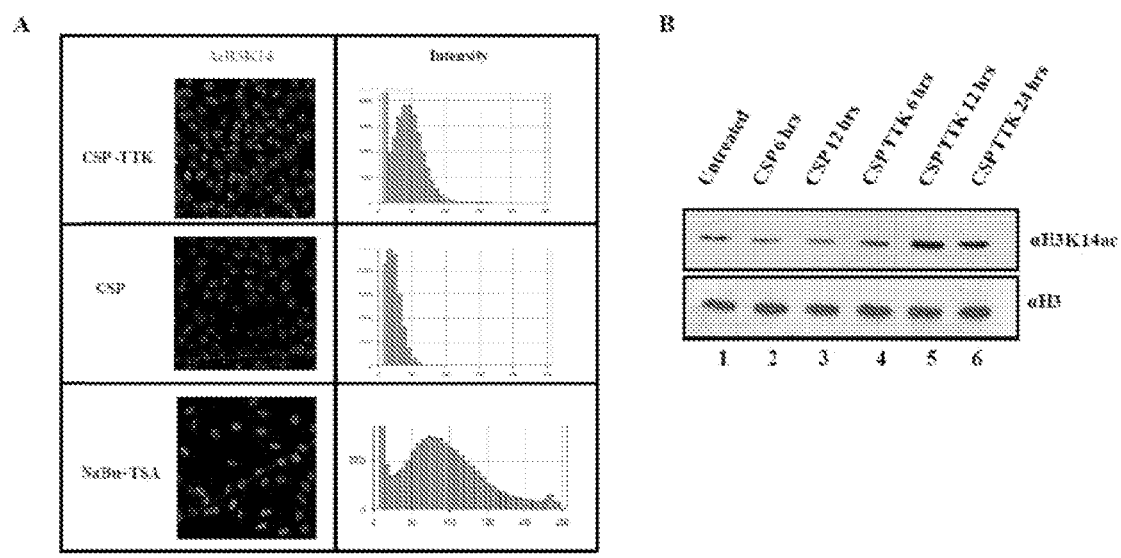

FIG. 8 depicts CSP-TTK21 inducing histone hyperacetylation in SHSY-5Y cells. (A) SHSY5Y cells are treated with CSP-TTK21 (500 μM), CSP (500 μM) and Sodium Butyrate (NaBu)+TSA (1 mM+2 μM respectively) for 24 hours and histone acetylation is measured by immunofluorescence analysis using antibodies against acetylated H3K14. The numbers of cells crossing the arbitrary intensities is counted and an 'intensity versus absolute frequency' curve is plotted for each treatment; (B) Immunoblotting analysis of cells treated with CSP for 6 hours and 12 hours (lane 2 and 3 respectively) and CSP-TTK21 upon 6 hours, 12 hours and 24 hours of treatment (lanes 4, 5 and 6 respectively) using antibodies against acetylated H3K14. Immunoblotting with H3 is taken as loading control.

Figure 9:
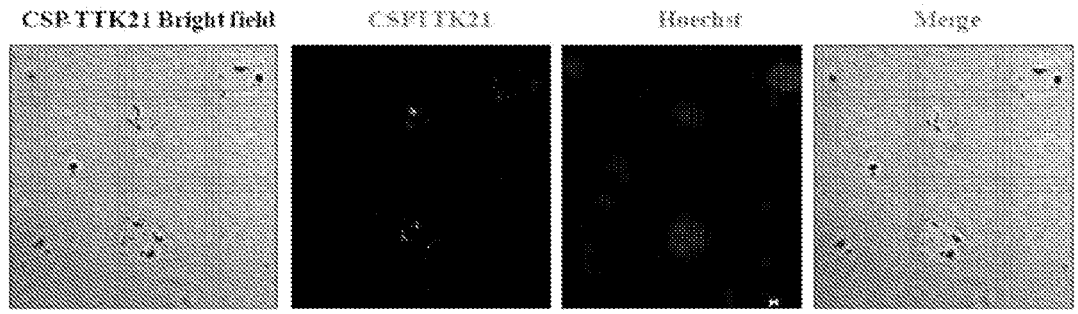

FIG. 9 depicts localization of CSP-TTK21 in mouse brain, 3 days after intra peritoneal injection of 250 m of CSP-TTK21. TTK21 conjugated to CSP is detected by excitation at 514 nm. Nucleus of the various cells in brain tissue is stained by Hoechst.

Figure 10:
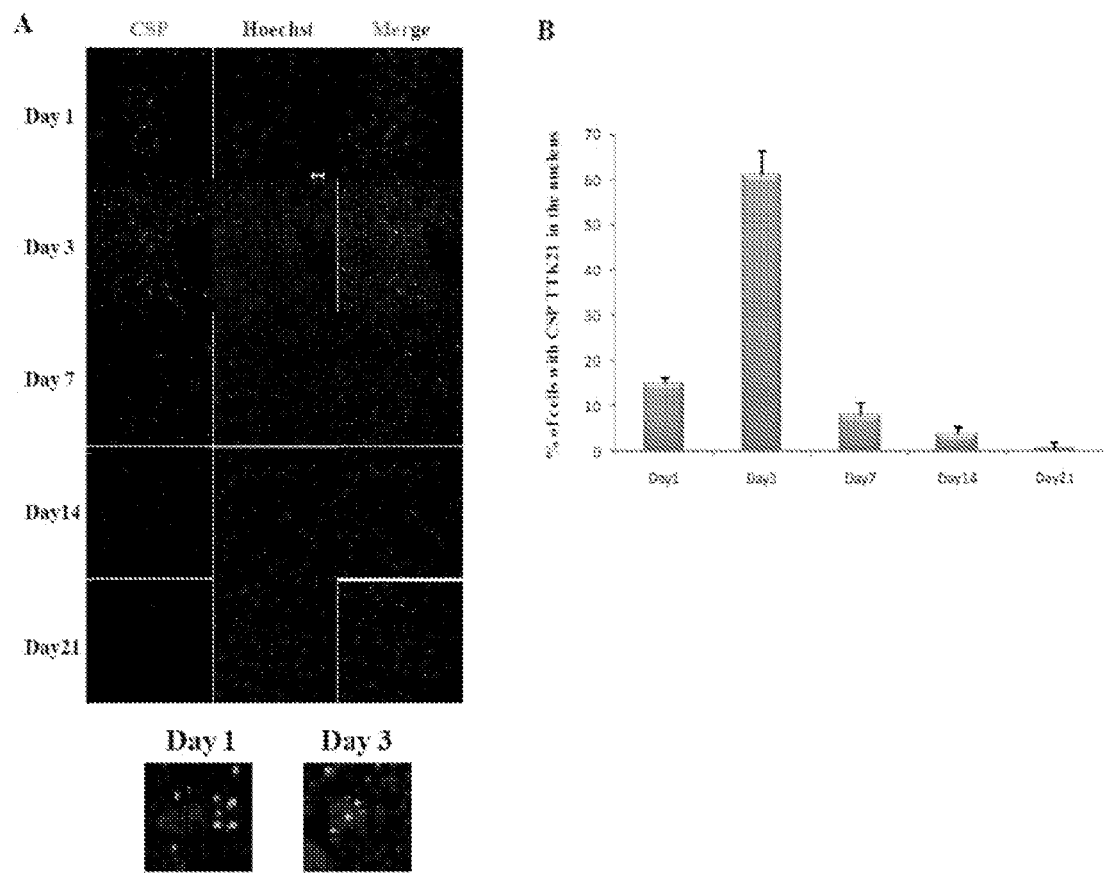

FIG. 10 depicts localisation of CSP-TTK21 following different times of intraperitoneal injection of CSP and CSP-TTK21 in cortex of mice brain, (A) 1-21 days after intra peritoneal injection of CSP-TTK21. CSP is detected by excitation at 514 nm. Nucleus of the cells in the cortex region of brain is stained by Hoechst. Maximum localization is observed on the 3rd day. Magnified image of the nucleus from day 1 and day 3 showing localization of CSP-TTK21 in the nucleus is also depicted (Below); (B) Quantification of the percentage of cells containing intra nuclear CSP-TTK21. Scale bar represents 10 μm.

Figure 11:
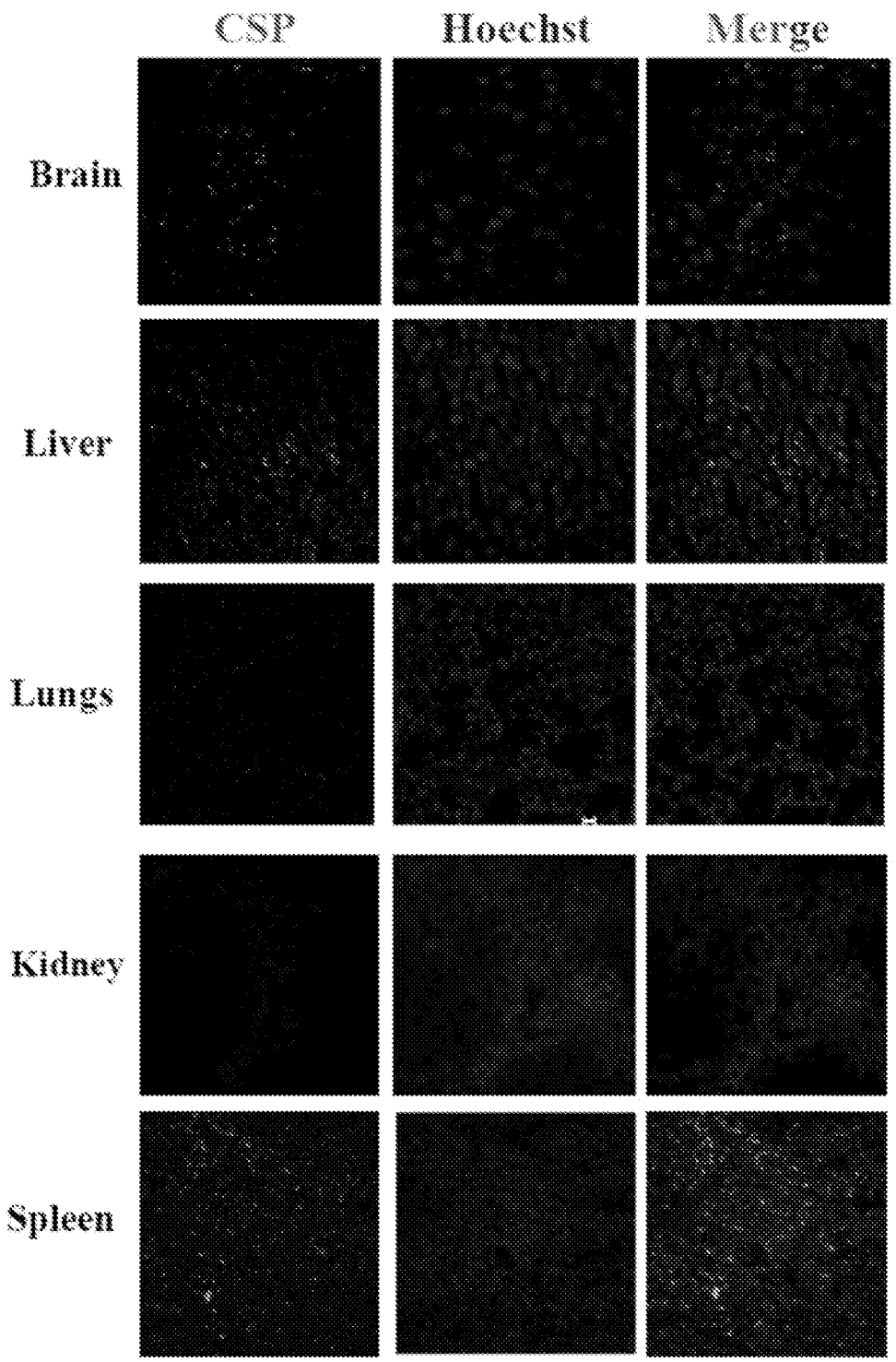

FIG. 11 depicts localization of CSP-TTK21 in different mouse organs at 1 day after intra peritoneal injection of 500 m of CSP-TTK21. TTK21 conjugated to CSP is detected by excitation at 514 nm. Nucleus of the cells in various tissues is stained by Hoechst. Scale bar represents 10 μm.

Figure 12:
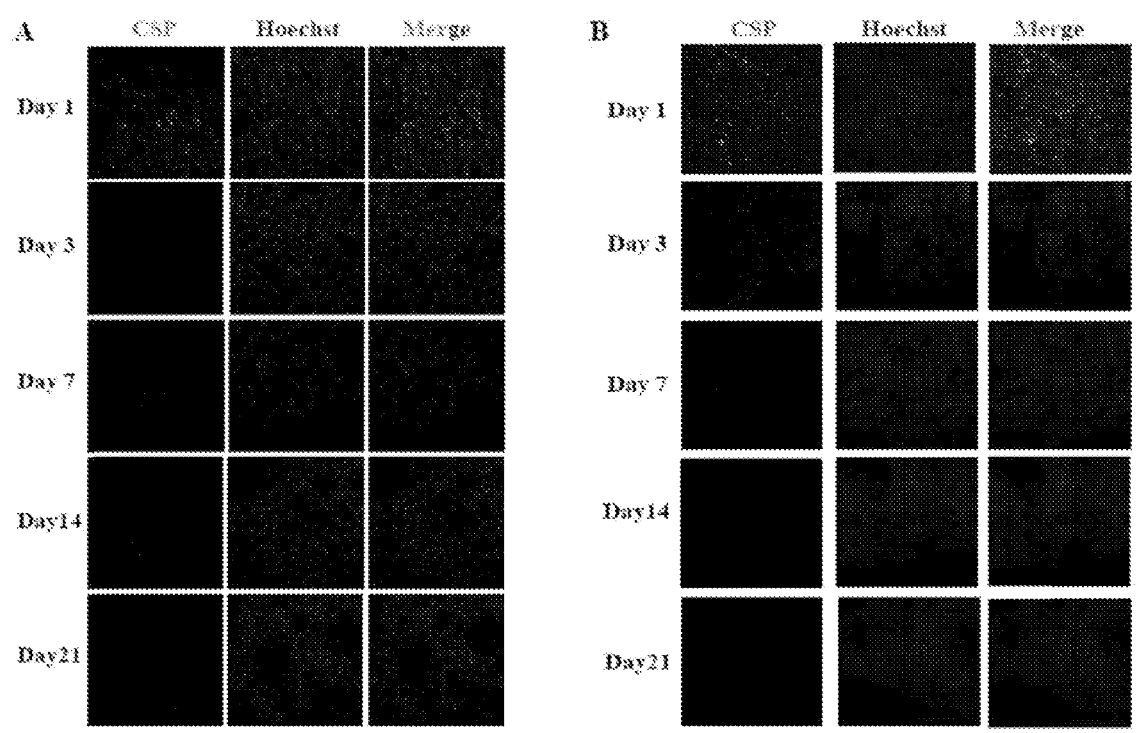

FIG. 12 depicts localisation of CSP-TTK21 in liver and spleen following different times of intraperitoneal injection of CSP and CSP-TTK21 composition in mice, 1-21 days after intra peritoneal injection of CSP-TTK21. CSP is detected by exciting at 514 nm. Nucleus of the cells in the liver (A) and spleen (B) is stained by Hoechst. Scale bar represents 10 μm. (C) Quantification for the percentage of CSP-TTK21 present in nucleus of cells after 3 days of injection.

Figure 13:
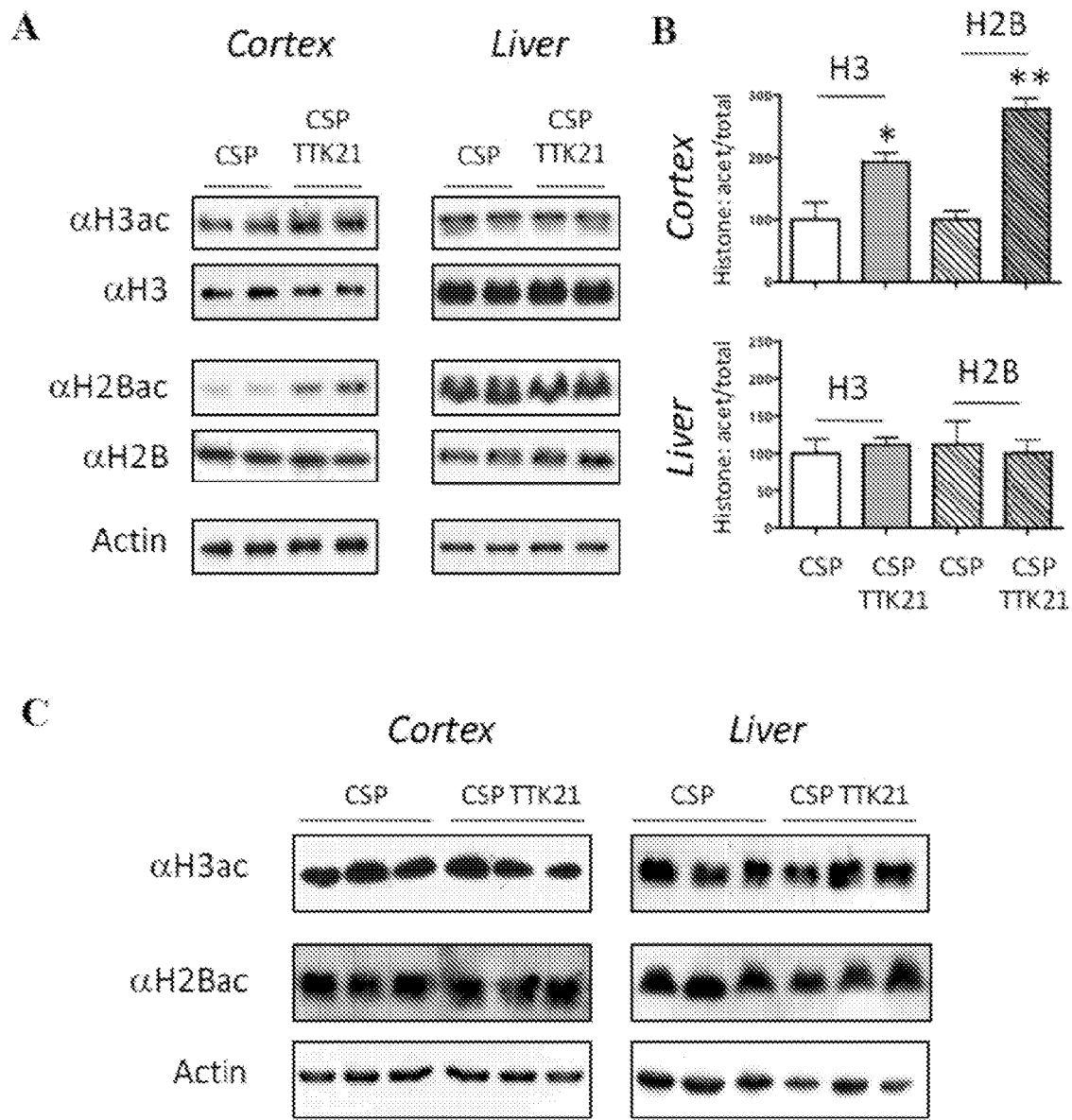

FIG. 13 depicts evaluation of histone acetylation levels in the cortex and liver following different times of intraperitoneal injection of CSP and CSP-TTK21 composition in mice. 500 μg of either CSP or CSP-TTK21 is injected intraperitoneally to Mice (n=4) and the mice are euthanized after 3 days (A) or 12 days (C). Brain and liver are dissected out and western blots are performed on total protein extracts with acetylated H3 (αH3ac), total H3 (αH3), with acetylated H2B (αH2Bac), total H2B (αH2B) or actin antibodies as indicated in the figure. Representative autoradiograms are shown (A and C). (B). Quantification of A (i.e. CSP-TTK21 injection to mice and euthanization after 3 days) in which acetylated histone (either H3 or H2B) is shown relative to the total amount of the respective histone. Student's t test, $*p<0.05$ and $**p<0.01$ when compared to CSP control.

Figure 14:
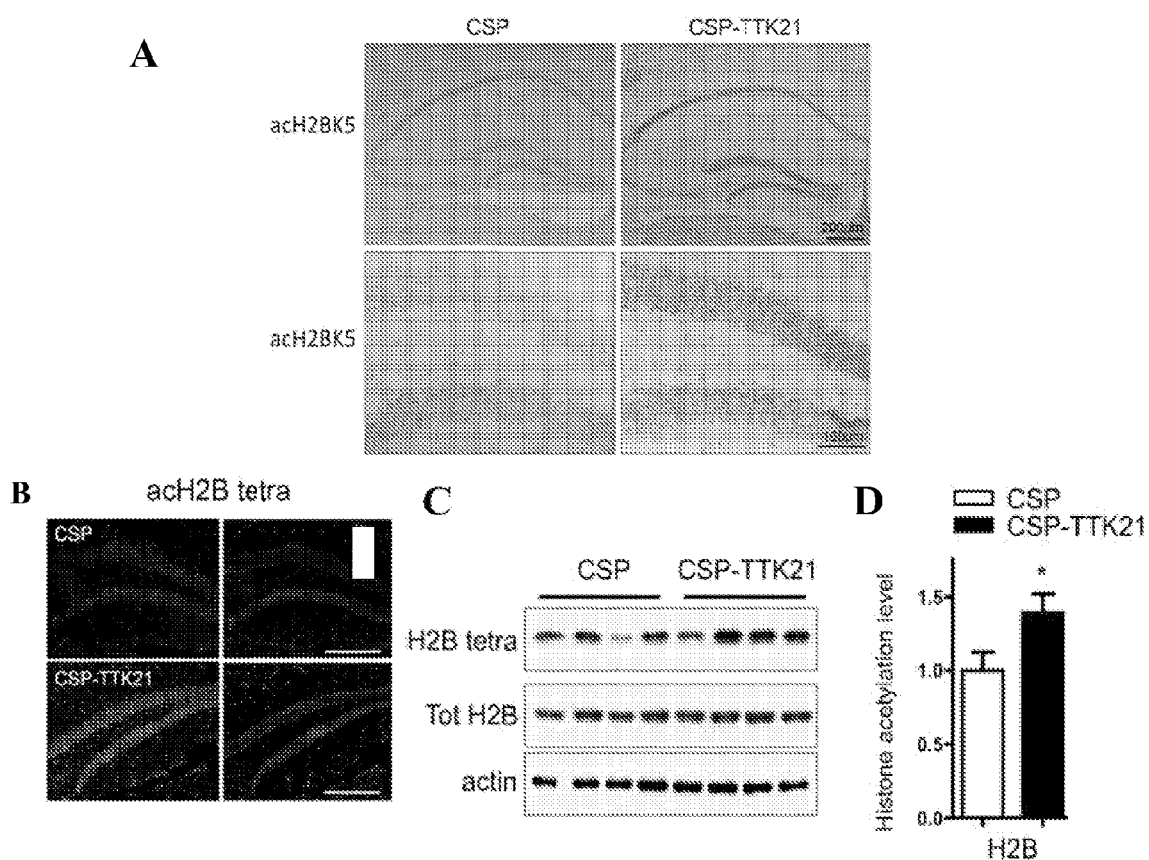

FIG. 14 depicts CSP-TTK21 induced hyperacetylation of histone H2B in hippocampus of mice brain. (A) Immunohistochemical analysis of mouse hippocampus 3 days after intraperitoneal injection of either CSP alone or CSP-TTK21 composition (500 mg each) using antibodies against acetylated histone H2B; (B) Immunofluorescence analysis of mouse hippocampus dentate gyms 3 days after intraperitoneal injection of either CSP alone or CSP-TTK21 composition (500 mg each) using antibodies against acetylated histone H2B. Hoechst dye is used to stain DNA of cells. (C) Immunoblotting of mouse hippocampal lysates using antibodies against acetylated H2B. Immunoblotting using antibodies against H2B is used as loading control; (D) Quantification fold of acetylation.

Figure 15:
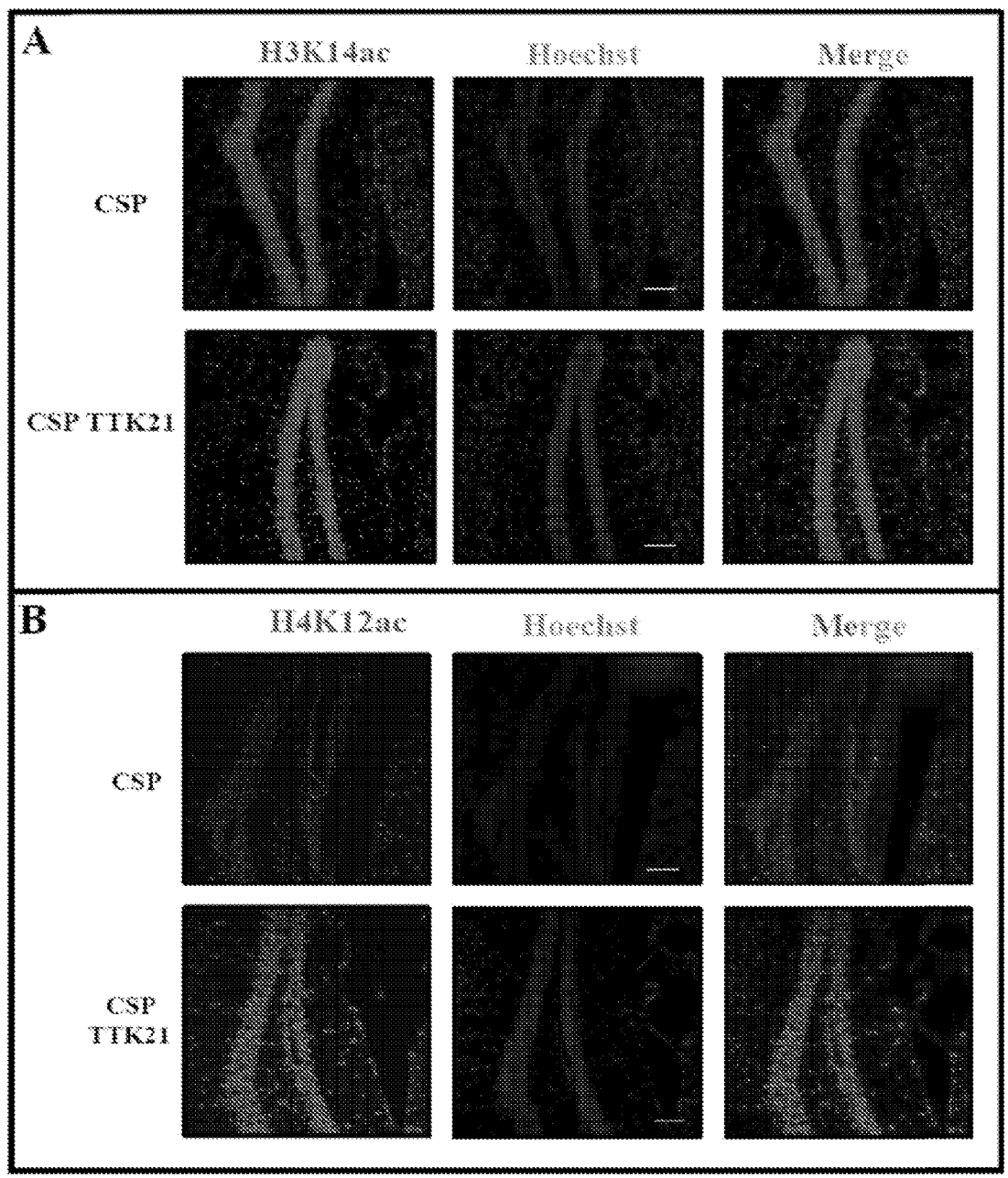

FIG. 15 depicts CSP-TTK21 induced hyperacetylation of histone H3 in dentate gyms of mice hippocampus. 500 μg of either CSP or CSP TTK21 is injected intraperitonially into mice and after 3 days the mice are sacrificed. Immunofluorescence assays of dentate gyms are performed using antibodies against: (A) acetylated H3K14 which show higher intensity in CSP-TTK21 mice tissue section and (B) acetylated H4K12 antibody. Scale bar represents 100 μm.

Figure 16:
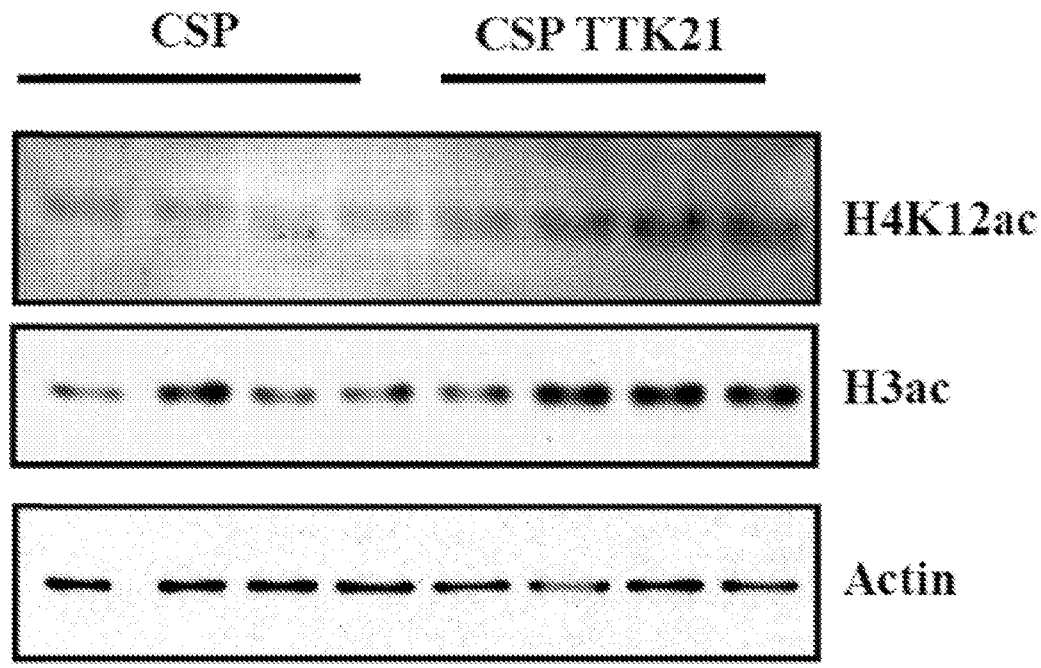
Figure 16:
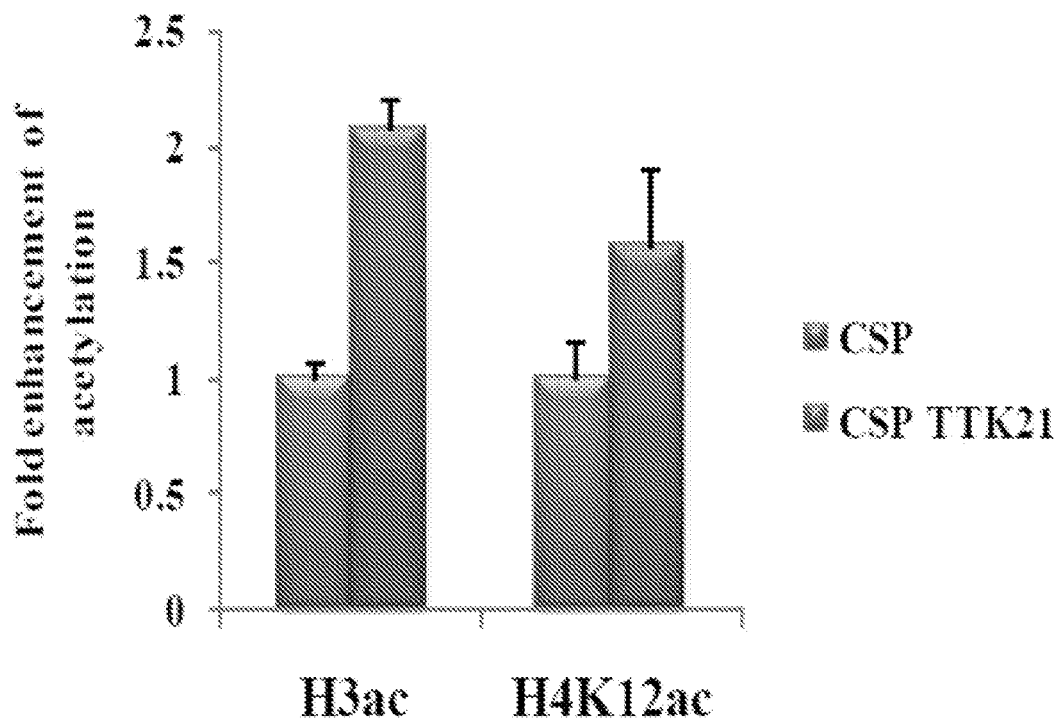

FIG. 16 depicts CSP-TTK21 induced hyperacetylation of histone H3 in hippocampus of mice brain. (A) Immunoblotting of mouse hippocampal lysates using antibodies against acetylated H3 and acetylated H4K12. Immunoblotting using antibody against β-Actin is used as loading control; (B) Quantification for fold enhancement of acetylation of histone H3 or H4K12 considering β-Actin as loading control.

Figure 17:
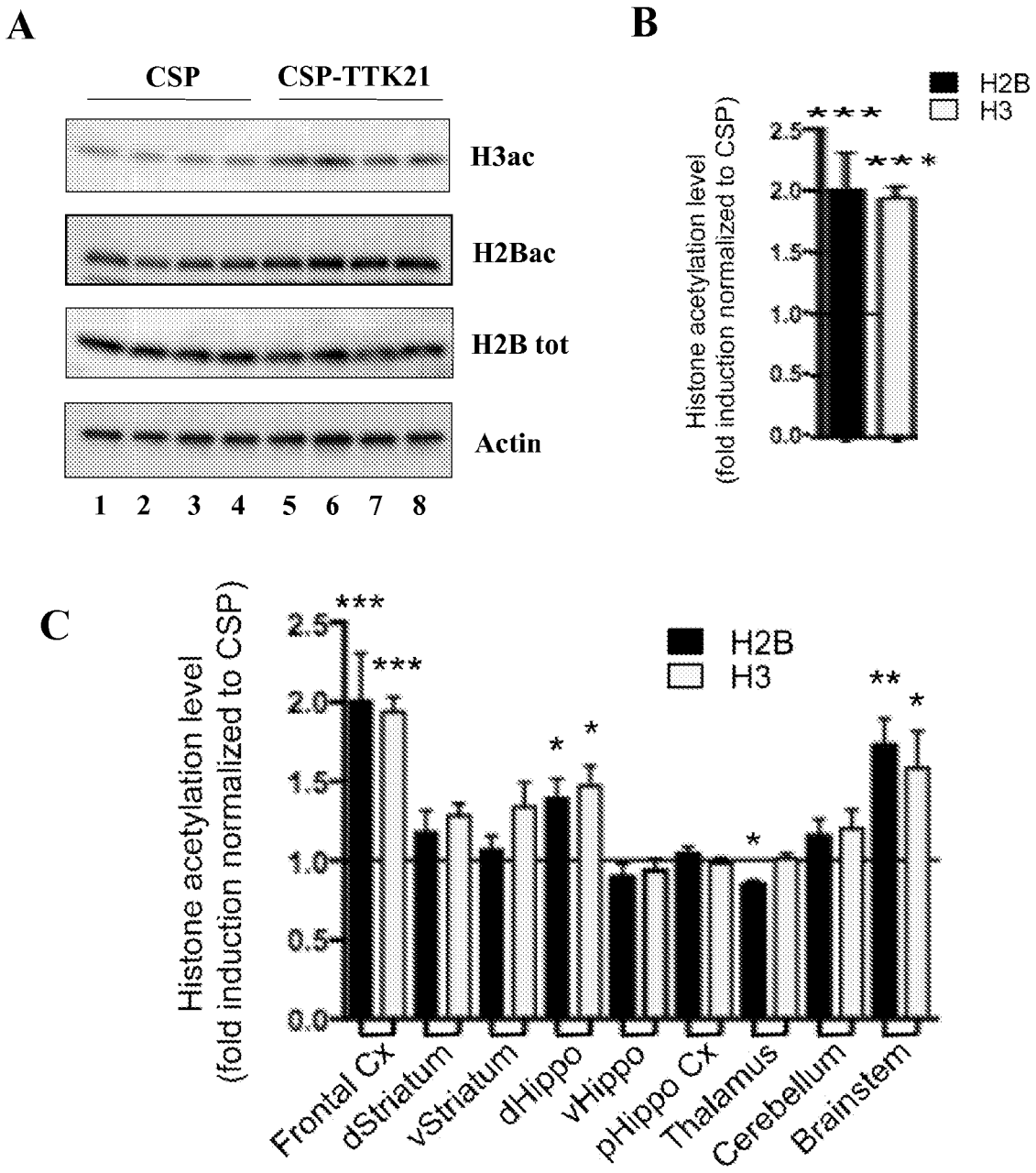

FIG. 17 depicts CSP-TTK21 induced hyperacetylation of histone H2B in prefrontal cortex of mice brain. 500 μg of either CSP or CSP TTK21 is injected intraperitonially into mice (n=4) and after 3 days, the mice are sacrificed. The prefrontal cortex is separated from the brain. Immunoblotting analysis is performed using antibody against (A) acetylated H2B and acetylated H3 with H2B total (H2B tot) as loading control; (B) Quantitative representation of the fold enhancement of H2B and H3 acetylation, n=4; Student's t test, $*p<0.05$ and (C) Three days after intraperitonial injection of either CSP alone or CSP-TTK21 (20 mg/kg of body weight), different organs or brain sub-regions are dissected out and western blots are performed on total protein extracts with acetylated-H2B or H3 and total H2B. Quantification of acetylated histone levels is shown relative to the total amount of the H2B (n=4-6). Student's t test, $*p<0.05$ and $p<0.01$ when compared to CSP control. # marks a result close to significance. Cx, cortex; d, dorsal; Hippo, hippocampus; v, ventral; p, para. $p<0.01$ when compared to CSP control.

Figure 18:
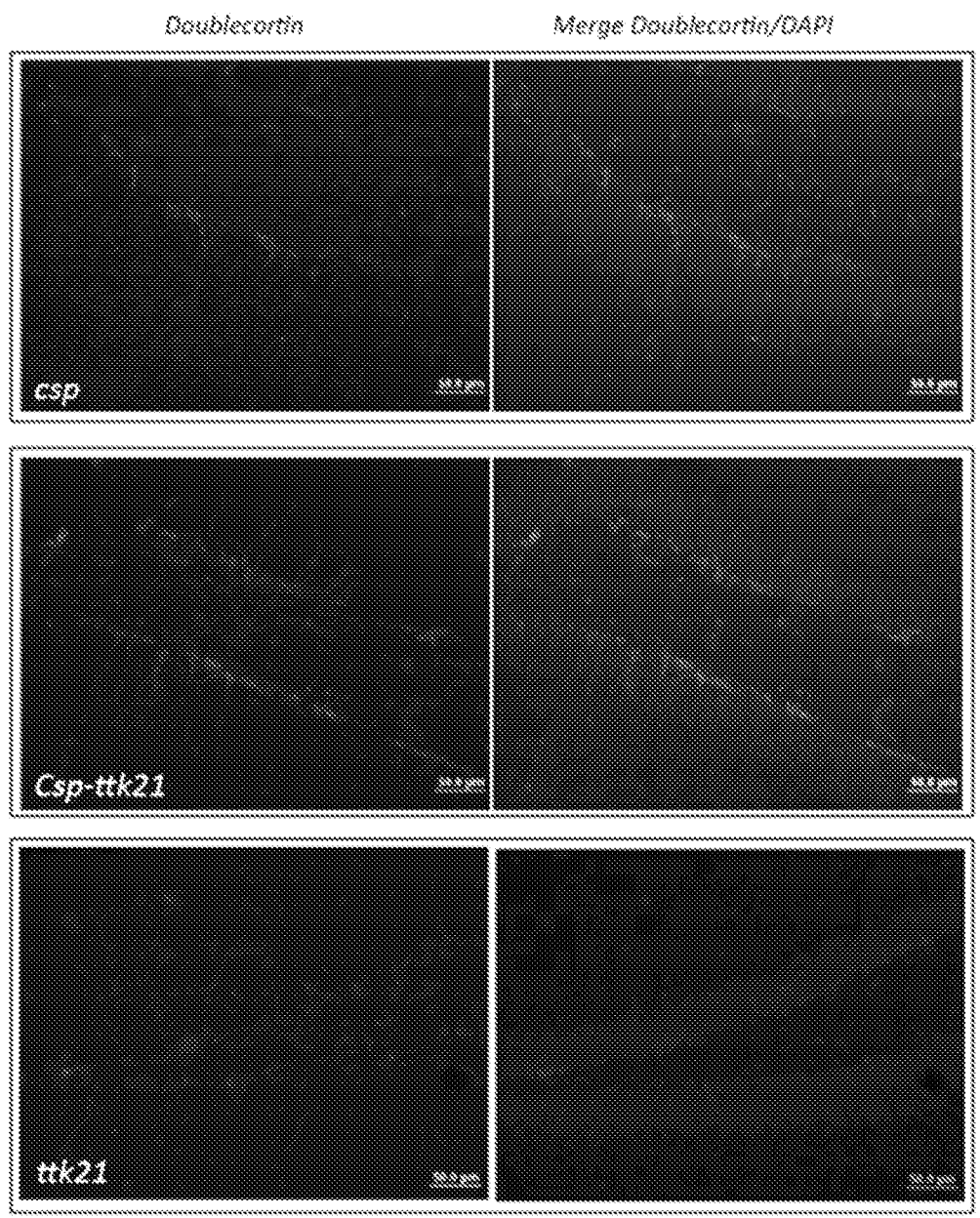

FIG. 18 depicts CSP-TTK21 induced neurogenesis in the inner wall of dentate gyms of mice hippocampus. 500 m of either CSP alone or TTK21 alone or CSP-TTK21 is injected intraperitonially into mice and after 3 days the mice are anesthetized and fixed with 4% paraformaldehyde. Brains are dissected out and post-fixed, cryoprotected and frozen. 20 μm thick sections are obtained and the results are analyzed by immunohistochemistry. Further, immunofluorescence assays are performed using antibody against double cortin. Scale bar represents 50 μm.

Figure 19:
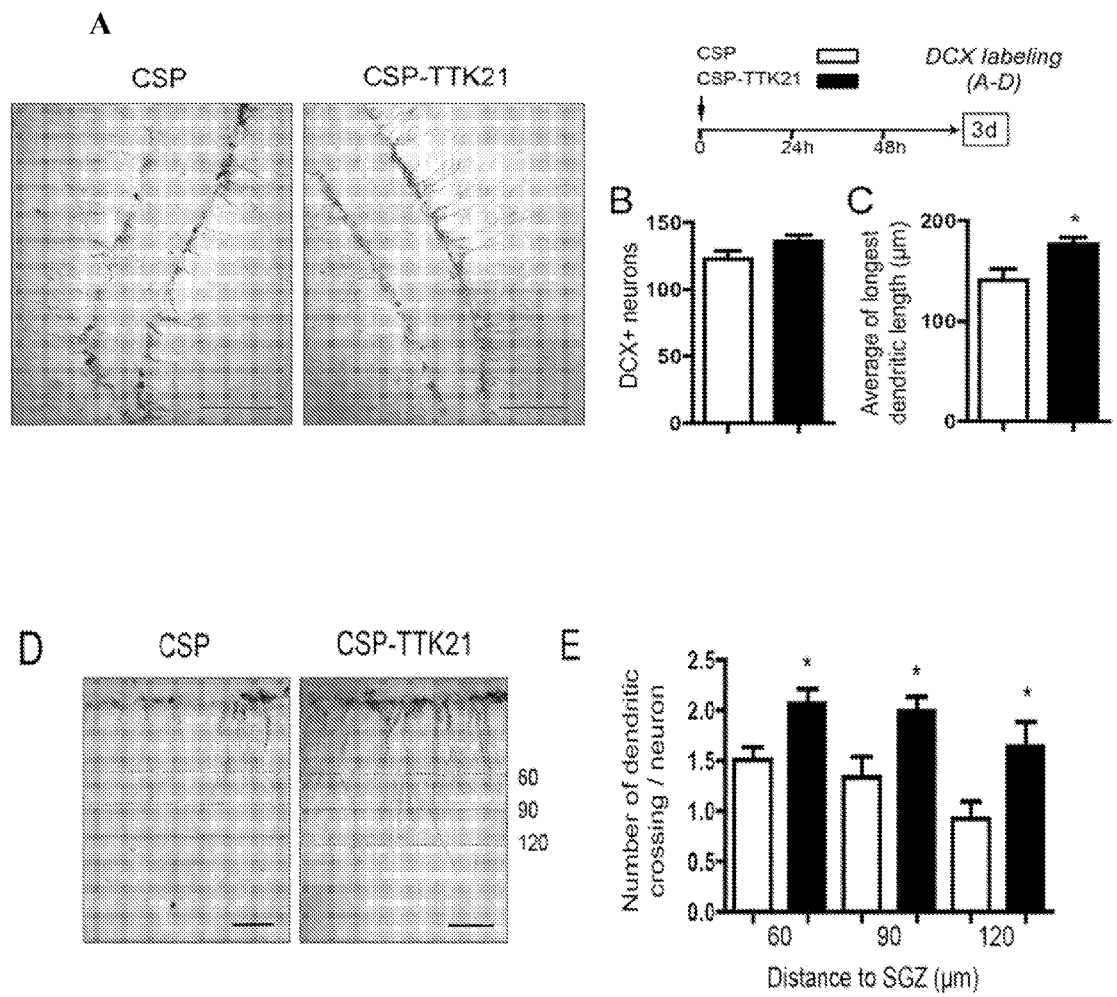

FIG. 19 depicts CSP-TTK21 induced neurogenesis in the inner wall of dentate gyms of mice hippocampus.

A-D, Immunohistochemistry analysis of the dentate gyms of mice, 3 days after intraperitonial injection of either CSP alone or CSP-TTK21 (20 mg/kg of body weight) using an antibody against doublecortin (DCX) followed by DAB staining. A typical photograph is shown (A). Scale bars: 100 μm. The timeline for injection and euthanasia is shown. h, hour; d, day. (B) Histograms represent the number of DCX-positive neurons per section (4-6 sections/animal). (C) The average of the longest dendrites associated to all DCX positive-new neuron within one hippocampus is calculated and is represented as histogram for each condition (CSP: 141.1 μm vs. CSP-TTK21: 176.9 μm, *p=0.0177, 4-6 sections/animal). (D), (A) typical cropped image from A is shown, on which the number of dendrites crossing virtual lines drawned at 60, 90 and 120 μm from the SGZ was counted (n=5 images/animal). (E) Histograms represent the dendritic crossing per DCX-positive neuron averaged from 3 animals. Student's t test. *p<0.05. Scale bars: 100 μm. It is to be noted that dendritic branching is still dense at the very end of the dendrites in CSP-TTK21 when compared to CSP treated mice.

Figure 20:
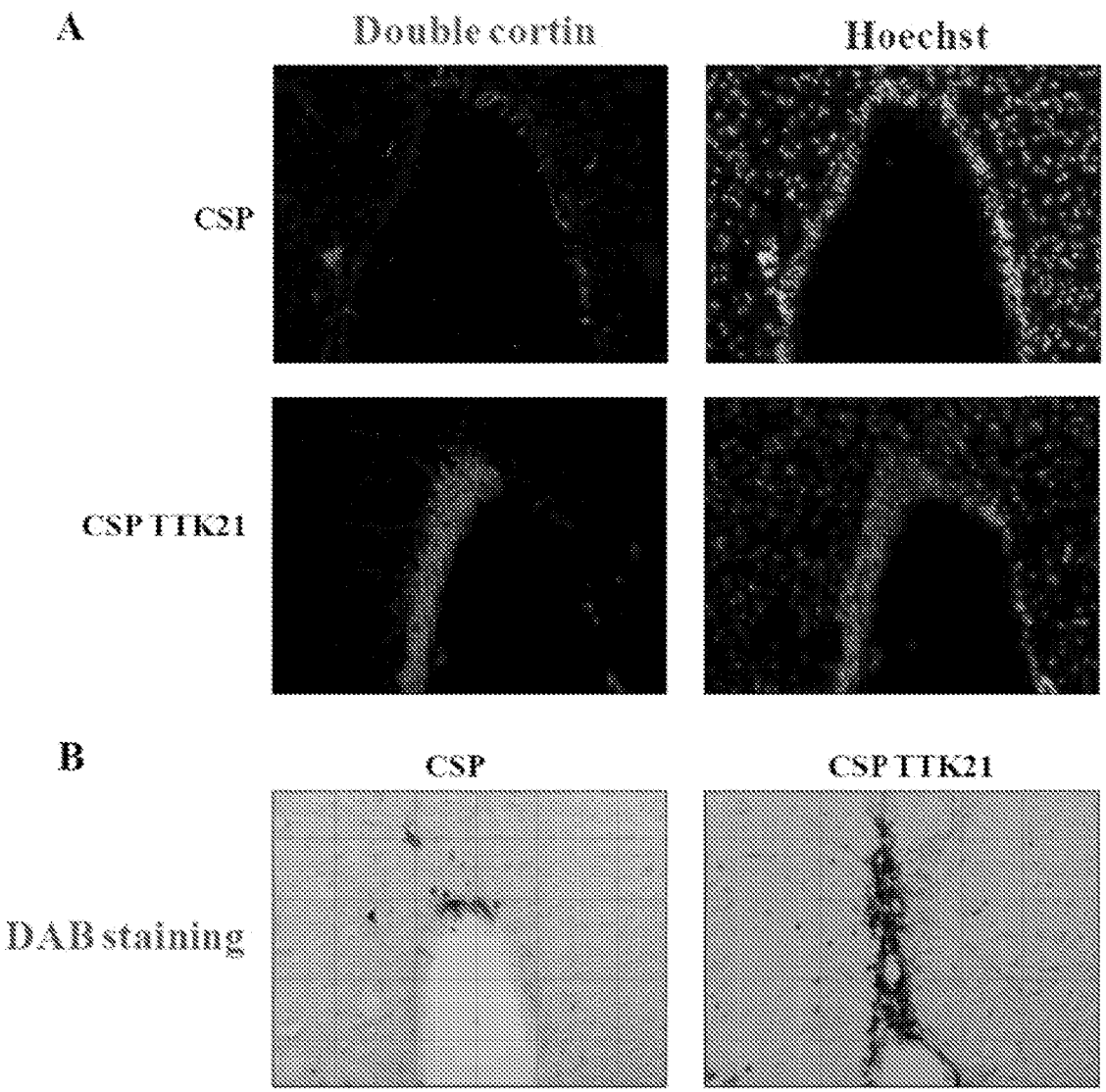

FIG. 20 depicts CSP-TTK21 induced neurogenesis in the sub ventricular zone (SVZ) of mice brain. 500 μg of either CSP or CSP TTK21 is injected intraperitonially into mice and after 3 days the mice are anesthetized and fixed with 4% paraformaldehyde. Brains are dissected out and post-fixed, cryoprotected and frozen. 20 μm thick sections are obtained and the results are analyzed by immunohistochemistry. (A) Immunofluorescence assays using antibody against double cortin; (B) Immunohistochemical assays using antibody against double cortin followed by DAB staining.

Figure 21:
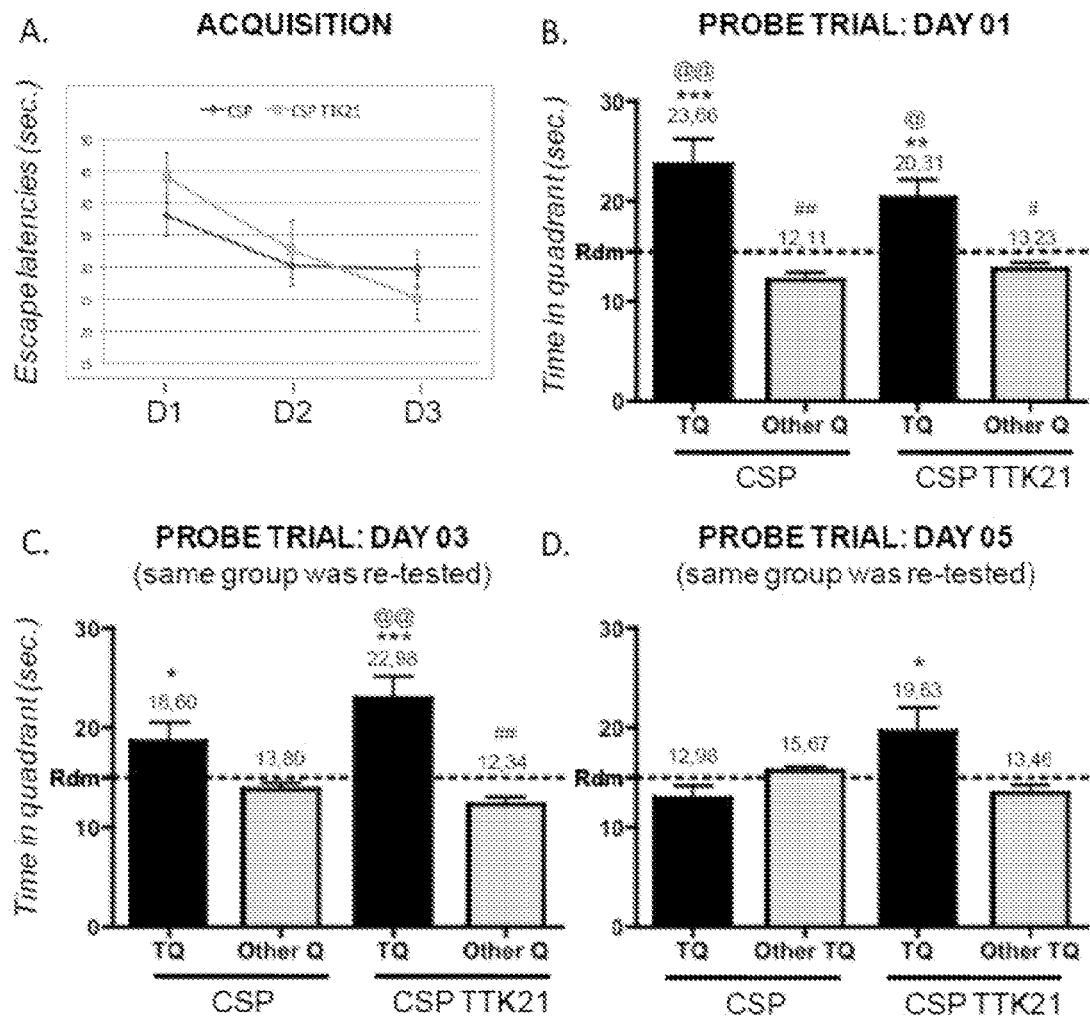

FIG. 21 depicts CSP-TTK21 induced persistent spatial memory. Mice (n=10/group) receive 500 μg of either CSP or CSP TTK21 injected intraperitoneally. Each group is subjected to a mild learning which consists of a 3-day acquisition training (4 trials per day) in the MWM (reference memory). Acquisition curves are presented in (A), as escape latencies (seconds) to reach the hidden platform. Mice are next subjected to 3 consecutive probe trials after 1, 3 and 5 days. Their retention performances are presented on (B), (C) and (D) respectively, as the time spent in the target quadrant (TQ) versus the mean of the 3 other quadrants (Other Q). Student 't test' with *p<0.05, p<0.01, *p<0.001 for TQ compared to Other Q. Student comparison to the standard random (Rdm, 15 seconds) with @ when significantly above and # when significantly below random. CSP-TTK21 treatment does not significantly change the memory abilities of the mice to retain the platform location 1 day after learning trials, but these treated mice do not present a classical extinction curve after different probe trials, as observed in CSP-treated mice: the trace seems more resistant to extinction.

Figure 22:
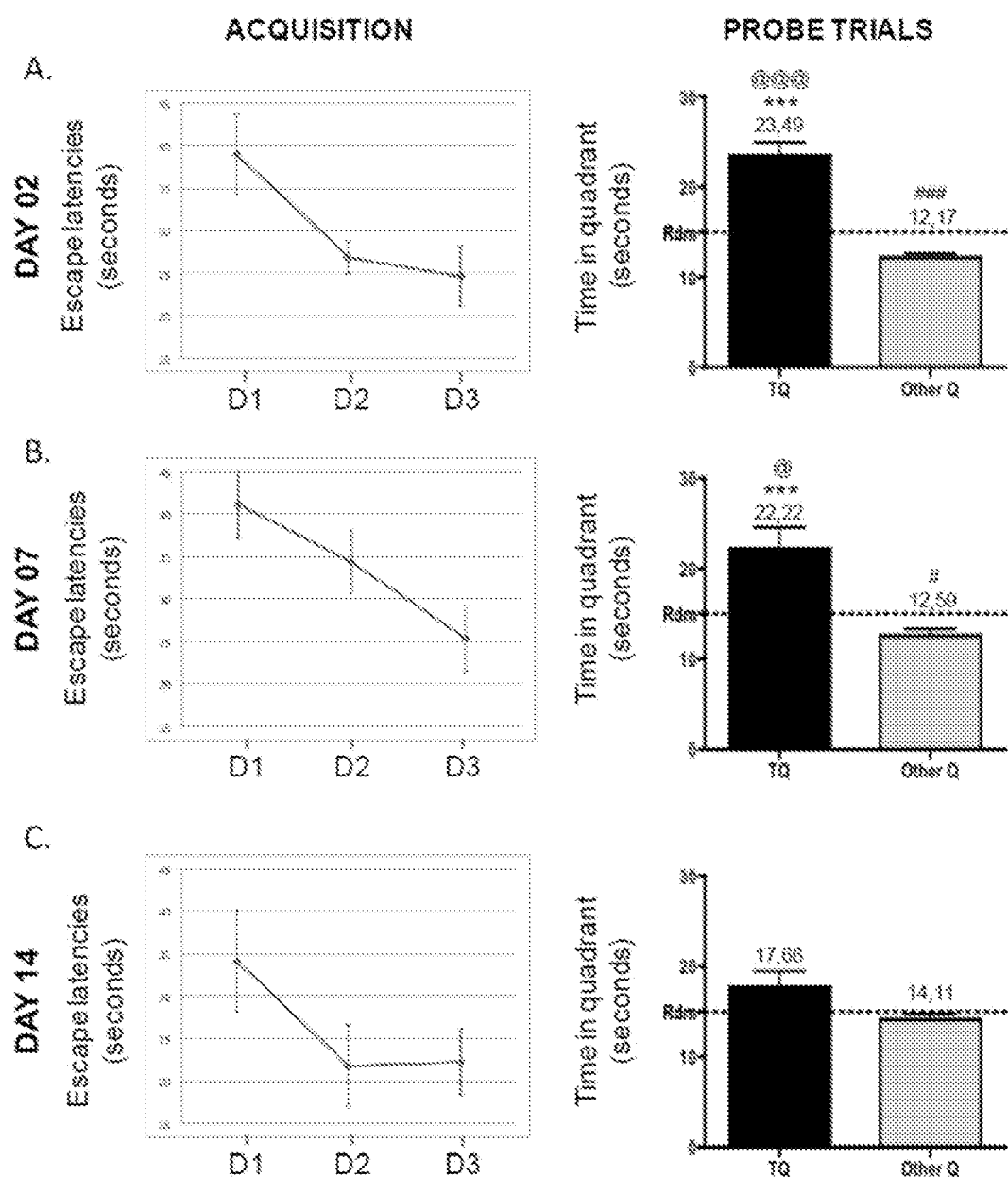

FIG. 22 depicts time course of retention performance after mild learning in mice when injected with CSP-TTK21. Mice (n=10/group are subjected to a mild learning as carried out in the experiments of FIG. 21. The different groups of mice are next subjected to one probe trial after 2, 7 or 14 days [ (A), (B) and (C) respectively]. Acquisition curves are presented in the left panels, as escape latencies (seconds) to reach the hidden platform and retention performances are presented on the right panels, as the time spent in the target quadrant (TQ) versus the mean of the 3 other quadrants (Other Q). Student 't test' with *p<0.05, p<0.01, *p<0.001 for TQ compared to Other Q. Student comparison to the standard random (Rdm, 15 seconds) with @ when significantly above and # when significantly below random. After a 3-day acquisition trial, mice show significant retention after 2 and 7 days, but no more after 14 days.

Figure 23:
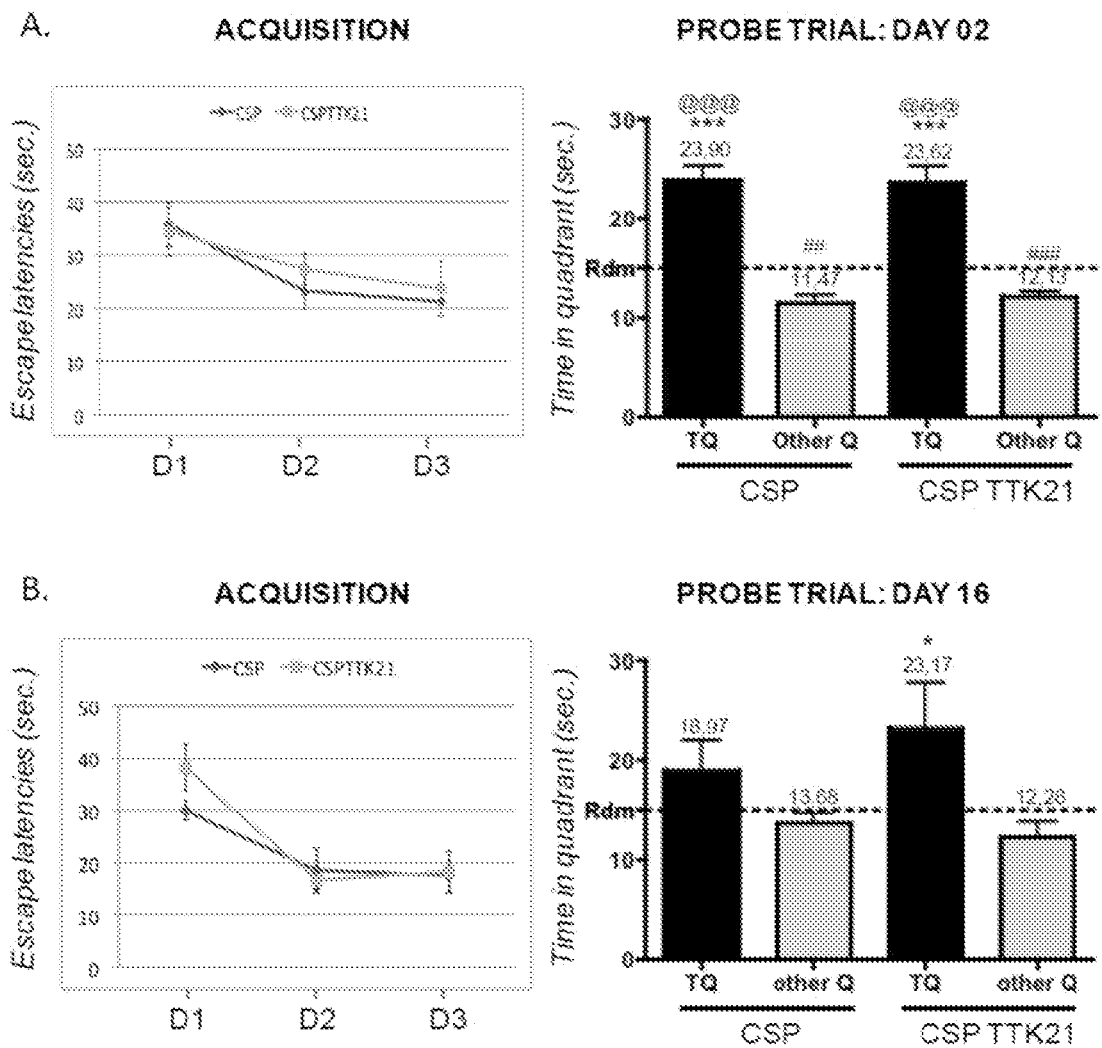

FIG. 23 depicts CSP-TTK21 induced remote spatial memory. Two groups of mice receive 500 μg of either CSP or CSP TTK21 injected intraperitoneally. Each group is separately subjected to a mild learning as described in FIG. 21. The first group is tested in a probe trial after 2 days (A) and the second group after 16 days (B) to assess for retention at a post-acquisition delay longer than in the former experiments (remote memory) (see FIG. 22). Acquisition curves of each group are presented in the left panels, as escape latencies (seconds) to reach the hidden platform. Retention performances are presented on the right panels, as the time spent in the target quadrant (TQ) versus the mean of the 3 other quadrants (Other Q). Student 't test' with *p<0.05, p<0.01, *p<0.001 for TQ compared to Other Q. Student comparison to the standard random (Rdm, 15 seconds) with @ when significantly above and # when significantly below random. While CSP TTK21 treatment does not change the ability of the mice to retain the platform location at the shorter time point (day 02), it enhances remote memory after 16 days.

Figure 24:
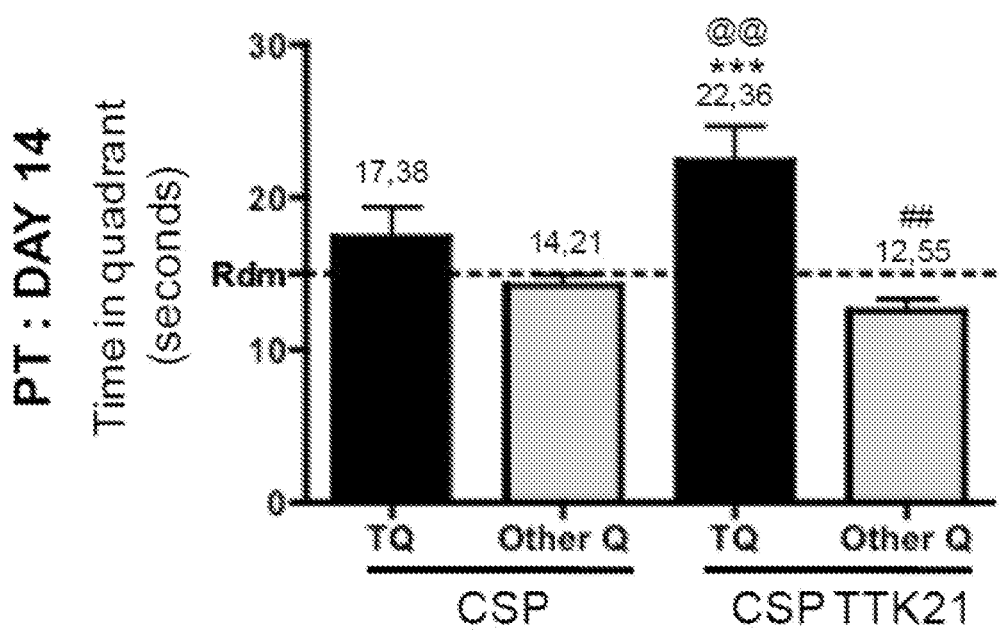
Figure 24:
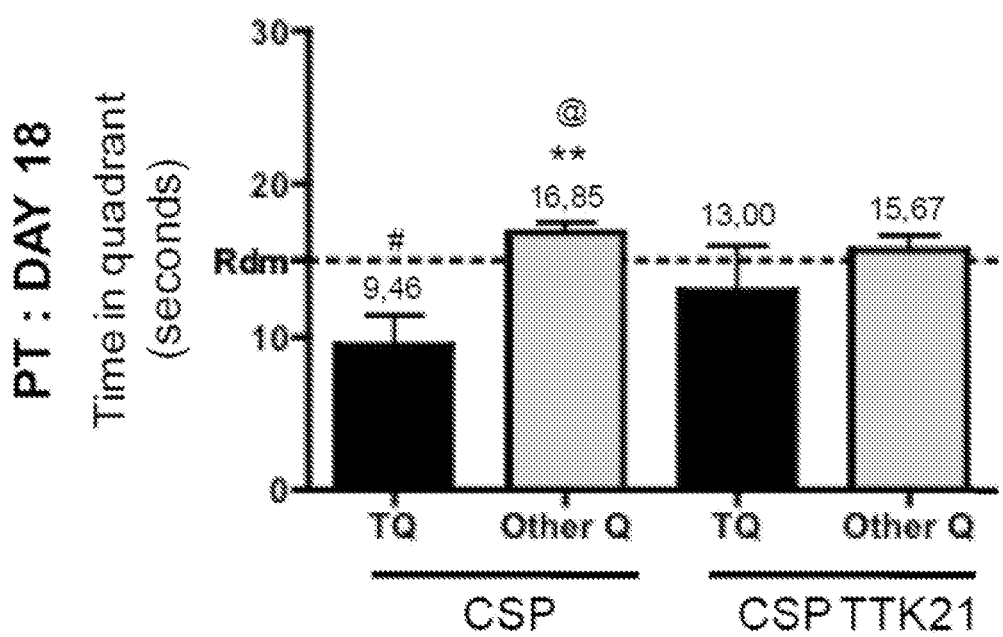

FIG. 24 depicts CSP-TTK21 induced persistent remote spatial memory. The two groups of CSP and CSP-TTK21 treated mice (n=10) that receive a 3-day acquisition training and a probe test at day 02 [see results on FIG. 22(A)] are further subjected to two more probe trials at day 14 (A) and Day 18 (B). Retention performances are indicated as the time spent in the target quadrant (TQ) versus the mean of the 3 other quadrants (Other Q). Student 't test' with * p<0.05, p<0.01, *p<0.001 for TQ compared to Other Q. Student comparison to the standard random (Rdm, 15 seconds) with @ when significantly above and # when significantly below random. CSP-TTK21 treated mice still remember the location of the hidden platform 14 days after acquisition and they do so despite the first probe trial performed on day 2, whereas CSP-treated mice forgot it. In a subsequent probe trial performed at day 18, none of the groups showed significant retention.

Figure 25:
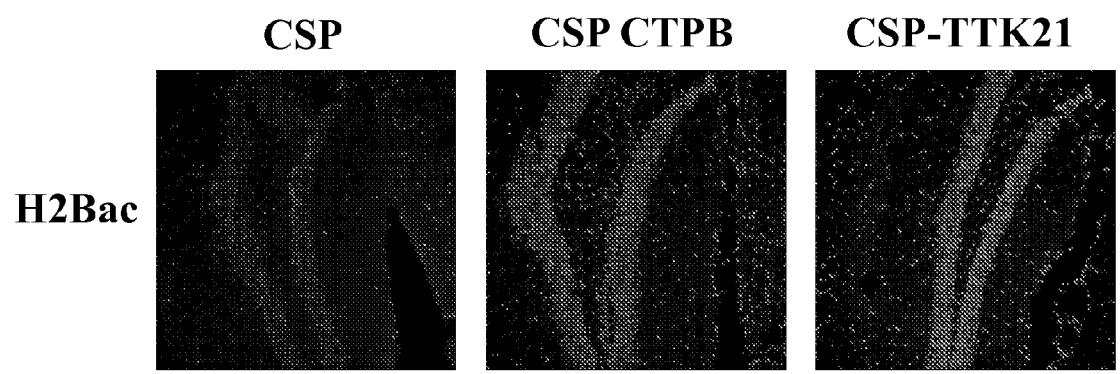

FIG. 25 depicts the comparison of activation of histone H2B acetylation by CSP alone, CSP-CTPB and CSP-TTK21 in hippocampus of mice brain. Mice are injected with either CSP alone, CSP CTPB or CSP-TTK21 (20 mg/kg each) and euthanized 3 days later. Immunofluorescent labeling of mouse dorsal hippocampus using antibodies against tetra-acetylated H2B.

Figure 26:
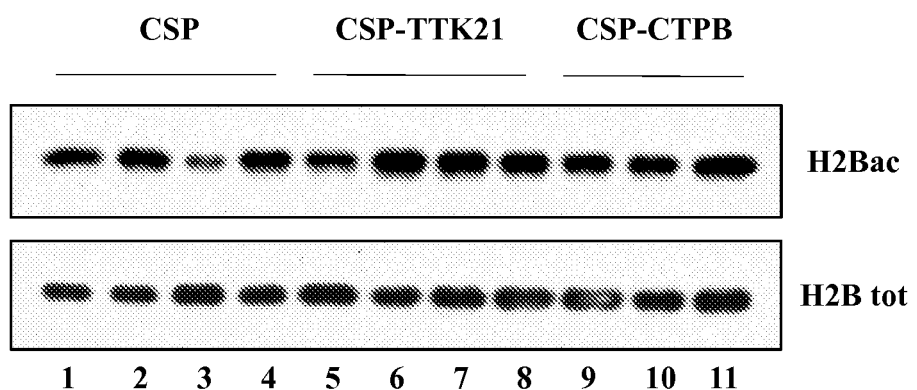
Figure 26:
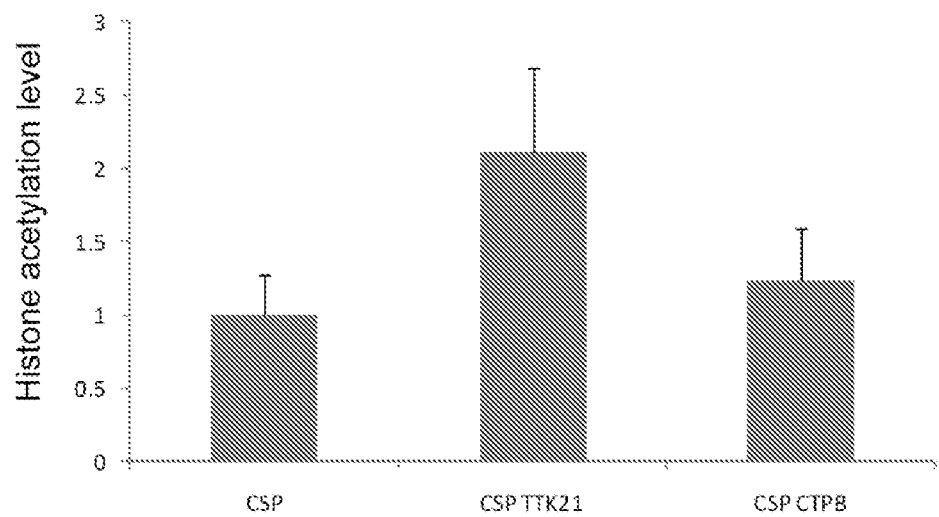

FIG. 26 depicts the comparison of activation of histone H2B acetylation by CSP alone, CSP-CTPB and CSP-TTK21 in hippocampus of mice brain. Mice are injected with either CSP alone, CSP CTPB or CSP-TTK21 (20 mg/kg each) and euthanized 3 days later. (A) Three days post-injection of either CSP alone, CSP-CTPB or CSP-TTK21 (20 mg/kg of body weight), dorsal hippocampi are dissected out and the total protein extracts are analyzed by western blots with antibodies against tetra-acetylated H2B histone. (B) Quantification of acetylated histone H2B is shown relative to the total amount of the H2B.

FIG. 27 depicts the comparison of activation of histone H3 acetylation by CSP alone, CSP-CTPB and CSP-TTK21 in hippocampus of mice brain. Mice are injected with either CSP alone, CSP-CTPB or CSP-TTK21 (20 mg/kg each) and euthanized 3 days later. (A) Immunohistochemistry is performed on 20 μm-thick cryosections with an anti-acetylated H3 Lys 14 antibody. Acetylation is observed to be increased in all hippocampal areas. (B) Immunofluorescent labeling of mouse dorsal hippocampus using antibodies against acetylated H3 Lys 14. (C) Three days post-injection of either CSP alone, CSP-CTPB or CSP-TTK21 (20 mg/kg of body weight), dorsal hippocampi are dissected out and the total protein extracts are analyzed by western blots with antibodies against acetylated H3 and H4 histones. (D) Quantification of acetylated histone H3 and H4 is shown relative to the total amount of the H2B.

Figure 28:
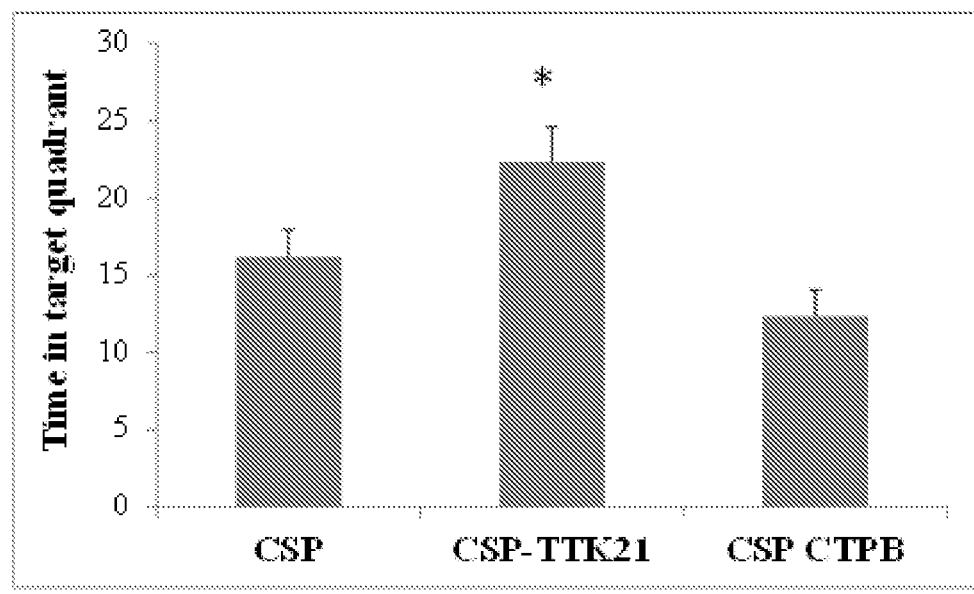

FIG. 28 depicts that HAT activator-induced acetylation by CSP-TTK21, but not CSP-CTPB or CSP alone in the brain extends memory duration. Three groups of mice (n=10/group) are trained using a Morris water maze protocol for only 3 days to ensure a "weak learning" (i.e. leaving possibilities of amelioration). Left: Acquisition performance is shown as latencies to reach the platform. Right: Mice are tested for retention in a probe trial performed after 16 days (16 d) after the last training session. The time spent in the target quadrant is represented. The mice injected with CSP-TTK21 show significant retention performance at day 16 compared to CSP or CSP CTPB injected mice [the figure depicts time in target quadrant (in seconds)]. Student's t test, *p<0.05 when compared to CSP control.

Figure 29:
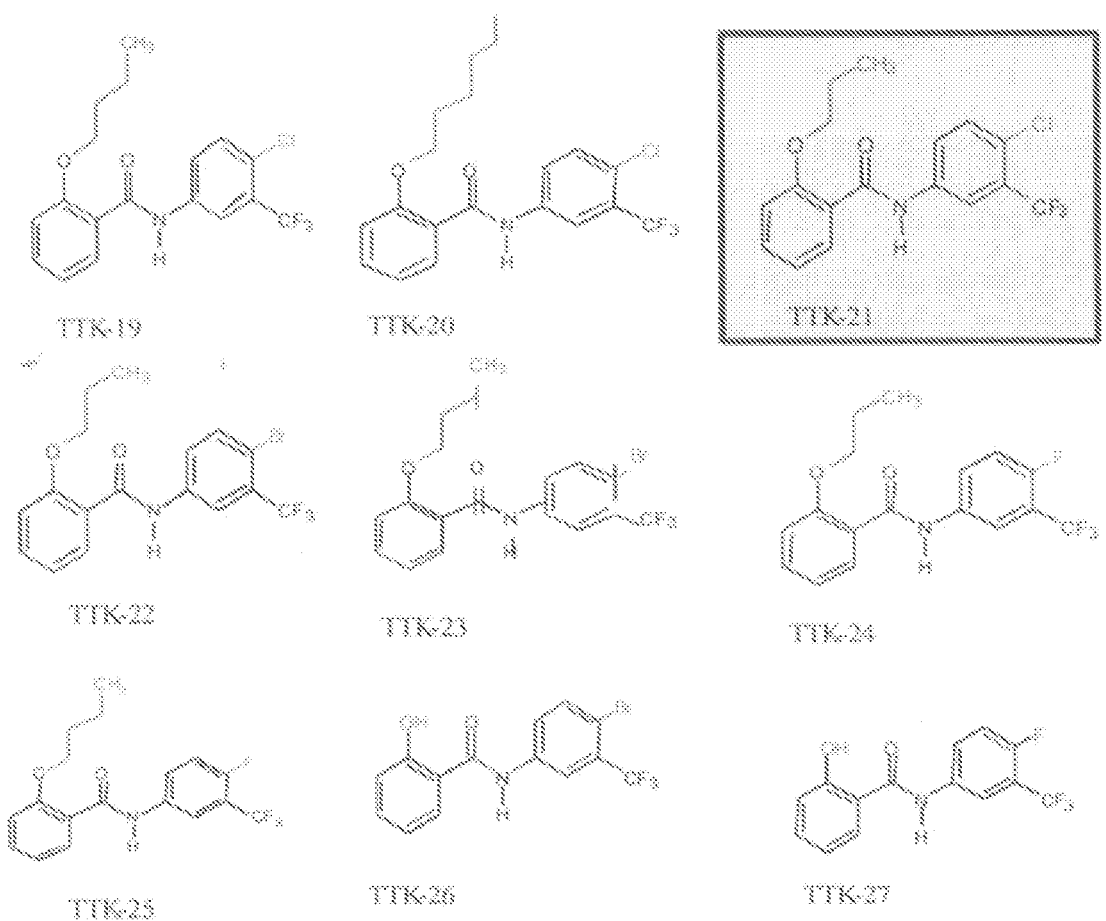
Figure 29:
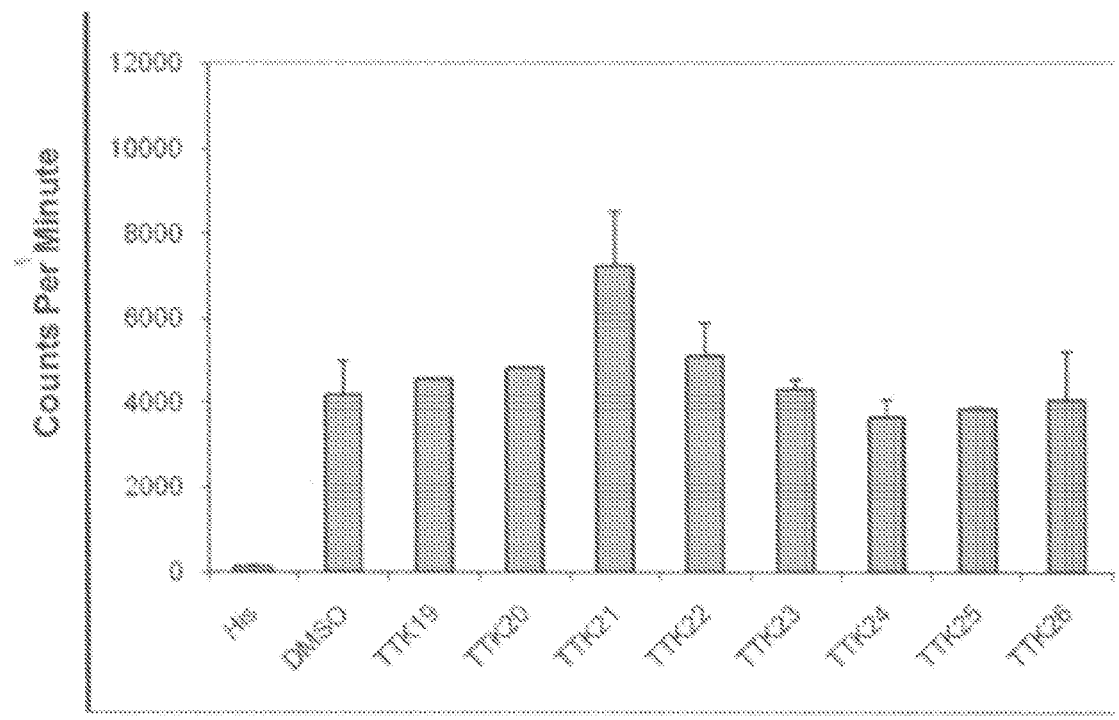

FIG. 29 depicts various derivatives of CTPB and their respective HAT modulatory activities. (A) Structures of CTPB derivatives (TTK19 to TTK27), and (B) HAT activation assay results.

DETAILED DESCRIPTION OF THE DISCLOSURE

The present disclosure relates to a composition comprising nanosphere and histone acetyltransferase (HAT) activator, wherein the HAT activator is N-(4-Chloro-3-trifluoromethyl-phenyl)-2-n-propoxy-benzamide.

In an embodiment of the present disclosure, the nanosphere is an intrinsically fluorescent carbon nanosphere (CSP) and the N-(4-Chloro-3-trifluoromethyl-phenyl)-2-n-propoxy-benzamide is covalently conjugated with said carbon nanosphere.

The present disclosure further relates to a process for obtaining a composition comprising nanosphere and histone acetyltransferase (HAT) activator, wherein the HAT activator is N-(4-Chloro-3-trifluoromethyl-phenyl)-2-n-propoxy-benzamide, said process comprising act of conjugating the N-(4-Chloro-3-trifluoromethyl-phenyl)-2-n-propoxy-benzamide with the nanosphere to obtain said composition.

In an embodiment of the present disclosure, the N-(4-Chloro-3-trifluoromethyl-phenyl)-2-n-propoxy-benzamide is obtained by a process comprising steps of:
  a) reacting salicyclic acid (A) with iodopropane (B) in presence of acetone and potassium carbonate to obtain propyl 2-propoxy-benzoate (C);
  b) reacting the propyl 2-propoxy-benzoate obtained in step (a) with potassium tertiary butoxide in presence of dimethyl sulfoxide to obtain 2-propoxy-benzoic acid (D);
  c) reacting the 2-propoxy-benzoic acid obtained in step (b) with thionyl chloride in presence of dimethylformamide and dichloromethane to obtain 2-propoxy-benzoyl chloride (E); and
  d) converting the 2-propoxy-benzoyl chloride in presence of 5-amino-2-chloro benzotriflouride to obtain the N-(4-Chloro-3-trifluoromethyl-phenyl)-2-n-propoxy-benzamide.

In another embodiment of the present disclosure, the conjugation is covalent conjugation; and wherein, the conjugation comprises steps of:
  a) adding N-(4-Chloro-3-trifluoromethyl-phenyl)-2-n-propoxy-benzamide to a solution containing nanosphere in presence of thionyl chloride, dimethylformamide and dichloromethane to obtain a reaction mixture; and
  b) stirring the reaction mixture at a temperature ranging from about 28° C. to about 30° C., for a time-period ranging from about 8 hours to about 9 hours to obtain the composition.

In yet another embodiment of the present disclosure, the step (b) of conjugation as described above further comprises steps of evaporation, washing and centrifugation and the composition is dried at a temperature ranging from about 50° C. to about 70° C., for a time-period ranging from about 2 days to about 3 days.

The present disclosure further relates to a method of inducing acetylation of histone by histone acetyltransferase (HAT), said method comprising act of contacting said histone acetyltransferase (HAT) with a composition comprising nanosphere and histone acetyltransferase (HAT) activator wherein the HAT activator is N-(4-Chloro-3-trifluoromethyl-phenyl)-2-n-propoxy-benzamide, for inducing the acetylation of histone.

In an embodiment of the present disclosure, the composition induces histone acetylation in organs selected from group comprising brain, liver and spleen or any combination thereof.

In another embodiment of the present disclosure, the composition induces histone acetylation in the brain by crossing blood brain barrier and entering nucleus of brain cells.

The present disclosure further relates to a method of inducing neurogenesis or enhancing long-term memory formation or a combination thereof, said method comprising act of administering in a subject, a composition comprising nanosphere and histone acetyltransferase (HAT) activator wherein the HAT activator is N-(4-Chloro-3-trifluoromethyl-phenyl)-2-n-propoxy-benzamide.

In an embodiment of the present disclosure, the composition induces neurogenesis or enhances long-term memory formation by crossing blood brain barrier and inducing acetylation of histone in brain.

In another embodiment of the present disclosure, the histone is selected from a group comprising H2B, H3 and H4 or any combination thereof.

In yet another embodiment of the present disclosure, the histone acetyltransferase (HAT) is selected from a group comprising p300/CBP and PCAF (p300/CBP Associated factor) or a combination thereof.

In still another embodiment of the present disclosure, the nanosphere is an intrinsically fluorescent carbon nanosphere (CSP).

In the present disclosure, the term 'TTK21' is an internal designation and can be generally referred to as 'COMPOUND 1'. Hence, COMPOUND 1 is also represented as TTK21 and therefore, for sake of convenience, COMPOUND 1 and TTK21 may be used interchangeably within the scope of the present disclosure.

Further, various compounds disclosed in the present disclosure are provided by their internal designations (TTK19-TTK20; TTK22-TTK27) and the same are referred as follows:
COMPOUND 2=TTK19
COMPOUND 3=TTK20
COMPOUND 4=TTK22
COMPOUND 5=TTK23
COMPOUND 6=TTK24
COMPOUND 7=TTK25
COMPOUND 8=TTK26
COMPOUND 9=TTK27

Hence, the above referred names may be used interchangeably within the scope of the present disclosure.

HATs (histone acetyltransferases) are an essential component for activation of chromatin transcription. Histone deacetylase (HDAC) inhibitors indirectly induce lysine acetylation by inhibiting various lysine deacetylase enzymes. HDAC inhibitors can induce histone acetylation in the brain and has roles in memory formation. The major limitation of using HDAC inhibitors as a therapeutic agent is its lack of substrate specificity and incapability to cross the blood brain barrier for some of them. HAT activators can induce activity of HAT directly but like HDAC inhibitors, HAT activators too are unable to cross the blood brain barrier. The present disclosure discloses the synthesis of a HAT activator COMPOUND 1that specifically activates p300/CBP. After the conjugation of COMPOUND 1 with the carbon nanospheres (CSP), the said CSP-COMPOUND 1 conjugate is able to efficiently cross the blood brain barrier and enter in mice brain.

The present disclosure discloses chemically conjugated N-(4-Chloro-3-trifluoromethyl-phenyl)-2-n-propoxy-benzamide (TTK21 or COMPOUND 1), a derivative of N-(4-Chloro-3-trifluoromethyl-phenyl)-2-ethoxy-6-pentadecyl-benzamide [CTPB] with the specific nanocarrier CSP to provide for a CSP-COMPOUND 1 composition which provides for more efficient delivery in the brain. This conjugated CSP-COMPOUND 1 induces acetylation of histones in the hippocampus and prefrontal cortex. This conjugate also enhances neurogenesis in the subgranular zone (SGZ) of the dentate gyms of hippocampus and the subventricular zone (SVZ) throughout the lateral walls of the lateral ventricles. In an embodiment, several examples and evidences are provided in the present disclosure showing that CSP-COMPOUND 1 enhances spatial memory formation, particularly long term events sustaining remote memory that require systemic consolidation and implicate the integration of new neurons in the brain circuitry. This effect is due to the potency of CSP-COMPOUND 1 to induce neurogenesis and increase survival of newly produced neurons in the SGZ.

In an embodiment of the present disclosure, various aspects such as the synthesis of COMPOUND 1, conjugation of COMPOUND 1 with CSP to obtain CSP-COMPOUND 1 conjugate, studies pertaining to HAT assays (using COMPOUND 1 alone, CSP alone, CSP-COMPOUND 1 conjugate and CSP-CTPB conjugate for a comparison of histone acetylation activity), and studies pertaining the ability of CSP-COMPOUND 1 conjugate to enhance neurogenesis and long-term memory formation is disclosed. Said ability of inducing histone acetylation, neurogenesis and/or long-term memory formation by the CSP-COMPOUND 1 conjugate of the present disclosure is useful in managing various disorders.

As used herein, "management" or "managing" refers to preventing a disease or disorder from occurring in a subject, decreasing the risk of death due to a disease or disorder, delaying the onset of a disease or disorder, inhibiting the progression of a disease or disorder, partial or complete cure of a disease or disorder and/or adverse affect attributable to the said disease or disorder, obtaining a desired pharmacologic and/or physiologic effect (the effect may be prophylactic in terms of completely or partially preventing a disorder or disease or condition, or a symptom thereof and/or may be therapeutic in terms of a partial or complete cure for a disease or disorder and/or adverse affect attributable to the disease or disorder), relieving a disease or disorder (i.e. causing regression of the disease or disorder).

The present disclosure is further elaborated with the help of following examples and associated figures. However, these examples should not be construed to limit the scope of the present disclosure.

EXAMPLES

Example 1

Screening of CTPB Derivatives

To understand the mechanistic aspects HAT activation various small molecules are derivatized from CTPB. The initial tail less derivative of CTPB is nomenclatured as N-(4Chloro-3-trifluoromethy 1-pheny 1)-2-ethoxybenzamide [CTB]. CTB is further derivatized to TTK series of compounds (COMPOUNDS 1-9) (FIG. 29 A). These compounds are subjected to histone acetyltransferase assays (filter binding assay) to check for their ability to activate p300/CBP HAT. Core histones purified from HeLa nuclear pellet is used as the substrate and p300 purified from baculovirus infected Sf21 cells is used to determine the HAT modulation activity of these compounds. All compounds are used at a concentration of 200 µM in the HAT assays. TTK21 (COMPOUND 1) show significant increase in radioactivity counts compared to other compounds (FIG. 29 B).

Results: The HAT activation assays depict COMPOUND 1 to be one of the most efficient HAT activator when compared to other CTPB derivatives (COMPOUNDS 2-9) which show significantly low HAT activation efficiency. COMPOUND 1 is further used for conjugation with CSP and studied for HAT activation and subsequent histone acetylation in various organs such as brain, liver and spleen.

Example 2

Synthesis of COMPOUND 1

About 14.5 mmol of Salicyclic acid (A) is dissolved in acetone, and to the solution, about 43.4 mmol of Iodopropane (B) is added (FIG. 1). To the reaction mixture, about 43.4 mmol of anhydrous $K_2CO_3$ is added. The reaction mixture is refluxed at a temperature of about 70° C. to about 80° C. for about 3-4 hours. The reaction upon completion is evaporated in vacuum and worked up using ethyl acetate and water. The combined organic extract is dried over $NaSO_4$ and then evaporated. The crude product thus obtained is purified using ethyl acetate and hexane (at a ratio of about 1:20) as an eluent, to yield 94% of the pure product Propyl 2-propoxy-benzoate (C).

To a solution of C (about 9 mmol) in DMSO, Potassium tertiary butoxide (about 11 mmol) is added at a temperature of about 0° C. The reaction mixture is stirred at a temperature of about 0° C. and for a time-period of about 30 minutes, followed by stirring the reaction mixture at room temperature (RT) (of about 25° C.-30° C.) for 2-3 hours. The reaction upon completion is worked upon using ice cold water and then extracted with dichloromethane (DCM). The combined organic layer is dried over $NaSO_4$ and then evaporated. The crude product thus obtained is purified by recrystallization using ethanol as the solvent, to obtain 95% of the desired product 2-Propoxy-benzoic Acid (D).

A solution of D (about 3.3 mmol) in 10 ml DCM is cooled in ice. To the cooled solution, thionyl chloride ($SOCl_2$) (about 3.66 mmol) is added dropwise. To the reaction mixture, few drops of DMF is also added. The reaction mixture is refluxed for about 2 hours. The reaction upon completion is evaporated in vacuum to obtain crude product 2-Propoxy-benzoyl chloride (E). To this crude product dissolved in DCM, 5-amino-2-chlorobenzotriflouride (about 3.3 mmol) is added. The reaction mixture is refluxed for about 3-4 hours. The reaction upon completion is worked upon using water and DCM. The combined organic extract is evaporated in vacuum to yield crude product which is purified using recrystallization to yield the pure product COMPOUND 1 (TTK21) (92% yield).

Results

COMPOUND 1 is synthesized using salicylic acid as a substrate as depicted in FIG. 1. Dose dependent activation of p300 by COMPOUND 1 is checked using filter binding assays. The concentrations of COMPOUND 1 selected for this particular assay are 50 µM, 100 µM, 200 µM and 275 µM. COMPOUND 1 shows activation of p300 starting from 5004 with maximum activation at the range of 250-275 µM (FIG. 2A). Gel fluorography studies are also performed and COMPOUND 1 mediated activation of p300 is observed in a dose dependent manner with maximum activation at 275 µM concentration (FIG. 2B). These screening experiments are also repeated with full length FLAG-CBP (FIG. 3). Both filter binding assays and gel fluorography show a dose dependent activation of CBP by COMPOUND 1 with maximum activation at the concentration of 275 µM range (FIG. 3 A, and B).

Example 3

Cell Permeability of COMPOUND 1

To check the cell permeability of COMPOUND 1, HeLa cells are treated with increasing concentrations (50 µM, 100 µM, 200 µM and 275 µM) of COMPOUND 1 and after 24 hrs, the cells are harvested and histones are isolated. Western blot analysis using antibody against acetylated H3 shows no alteration of histone H3 acetylation upon treatment of COMPOUND 1 (FIG. 4, compare lane 1 with 3, 4, 5 and 6). This shows the inability of the COMPOUND 1 molecule itself to enter into mammalian cells.

The cell permeability tests of COMPOUND 1 alone is also carried out in various neural cell lines such as SHSY cells and the results are found to be similar to HeLa cells. In other words, the results depict the inability of the COMPOUND 1 molecule alone to enter into mammalian cells.

Example 4

Conjugation of Carbon Nanosphere (CSP) with COMPOUND 1

To a suspension of about 100 mg of CSP in DCM, 1 equivalent of $SOCl_2$ diluted in DCM is added dropwise, followed by the addition of few drops of DMF (FIG. 5). The reaction mixture is stirred at RT (about 28° C.-30° C.) for about 8-9 hours. To this solution, COMPOUND 1 dissolved in DCM is added dropwise. The reaction mixture is stirred for about 8-9 hours at RT (about 28° C.-30° C.). The solvent is then evaporated and later washed with cold water. The crude product is centrifuged and the supernatant i.e. water is removed. This procedure is repeated for about 7-8 times. Washing is then carried out using DCM, followed by the supernatant being tested for the absence of COMPOUND 1. The obtained CSP-COMPOUND 1 conjugate is then dried at a temperature of about 60° C. for a time-period of about 2-3 days.

Results

The intrinsically fluorescent and cell permeable carbon nanosphere (CSP) employed in the present disclosure has the ability to reach different organs like spleen, liver and brain. In order to develop an efficient device to activate the histone acetylation in the brain, a histone acetyltransferase activator based on salicylic acid (i.e. COMPOUND 1) is synthesized and has been covalently conjugated to the surface of CSP. The entire device has the ability to pass the liver and reach brain and induce histone acetylation.

For the chemical conjugation, the functional groups present on the surface of CSP are used (FIG. 5). The conjugation is confirmed by IR and EDX analysis (FIG. 6). The intrinsic fluorescence of CSP-COMPOUND 1 is checked under confocal laser scanning, where it is excited at 514 nm and the fluorescence is observed at 560 nm (FIG. 7).

In an embodiment, the covalent conjugation provides CSP-COMPOUND 1 more stability and uniformity for the number of COMPOUND 1 molecules attached on CSP surface. Also, the number of COMPOUND 1 per CSP molecules during the formation of CSP-COMPOUND 1 conjugate can be controlled.

Example 5

Histone Acetyltransferase (HAT) Assays

Highly purified HeLa core histones are incubated in HAT assay buffer at about 30° C. for a time-period of about 10 minutes with or without baculo virus expressed recombinant p300 or CBP in the presence or absence of small molecules (i.e. HAT activators). The incubation is followed by the addition of about 1 µl of 3.6 Ci/mmol $^3$H-acetyl CoA (NEN-PerkinElmer) and further incubation for about 10 minutes in a final volume of 30 µl at 30° C. The mixture is blotted onto P-81 (Whatman) filter paper and radioactive counts are recorded on a Wallac 1409 liquid scintillator counter. For gel fluorographic assays, histones are isolated by trichloroacetic acid (TCA) precipitation using 25% TCA. The pellet obtained is washed twice with acetone and dissolved in 2×SDS loading dye, heated for about 5 mins and is followed by separation using 15% SDS-PAGE. Comassie staining is performed to ascertain the presence of equal loading in each reaction and is later dehydrated in DMSO for about 1 hour. Dehydrated gel is later incubated in scintillation fluid (PPO solution in DMSO) for about 45 minutes and rehydrated again in distilled water for about 4 hours. The gel is then dried using a gel drier and later exposed in an X-ray cassette using a film for about 5 days in −80° cooler. The film is then developed to obtain the intensity profiles for each of the reactions.

Immunofluorescence in SHSY 5Y Cells

Cells are grown on a poly-Lysine coated coverslips at about 37° C. in a 5% $CO_2$ incubator. After indicated amount of treatment with molecules (CSP alone and/or CSP-COMPOUND 1) for indicated time-periods, cells are washed with PBS and fixed with 4% paraformaldehyde (in PBS) for about 20 minutes at room temperature. Cells are permeabilized using 1% Triton-X100 (in PBS) for about 10 minutes and washed thrice with PBS for about 10 minutes each. Non specific blocking is performed using 5% FBS (in PBS) for about 45 mins at about 37° C. Primary antibody is added in appropriate dilutions for about 1 hour at room temperature (of about 28° C.-30° C.). Cells are then washed with wash buffer (1% FBS in PBS) 4 times for 3 minutes each. Secondary antibody tagged with fluorescent dye is added in appropriate dilutions and incubated for about 1 hour at room temperature followed by washes with wash buffer. The nuclei are then stained with Hoechst (1:10,000 dilution) for about 20 minutes. PBS washes are carried out two times and the coverslips are inverted onto a microscopic slide over 2 µl of 70% glycerol (in PBS) and imaged using a confocal microscope.

Immunofluorescence for animal tissue Mice are injected with indicated amounts of the molecules (CSP alone, CSP-CTPB and/or CSP-COMPOUND 1) and after the defined time periods, they are deeply anesthetized with pentobarbital and perfused transcardially with 150 ml ice-cold paraformaldehyde (4% in 0.1M PB, 4° C.). Brains are then rapidly removed from the skull and post-fixed for about 6 hours in the same fixative at +4° C. Fixed brains are then kept in sucrose at about +4° C. for a time-period of about 48 hours. Freezing of the brains is then performed in isopentane for about 1 minute at a temperature of about −40° C. and stored in −80° C. freezer. Coronal sections of about 20 µm in thickness are made through the dorsal hippocampus using the vibratome (Leica VT1000M). CSP, CSP-CTPB and/or CSP-COM- POUND 1 treated mice brain sections are kept in a same poly lysine coated slides. The tissue sections are permeabilized in 1XPBS/Triton 2% for about 15 minutes. Non-specific labeling is blocked by employing 1XPBS/Triton 0.1%/horse serum 5% for about 30 minutes at about 37° C. The slices are then incubated overnight with the indicated antibodies in appropriate dilutions and then washed, followed by incubation with secondary antibody conjugated with fluorescent dye for about 1 hour. After three washes with 1XPBS/Triton 0.1%, the nuclei are stained with Hoechst (1:1000 dilutions) for about 5 mins. PBS washes are given for about two times and the stained nuclei are later mounted.

Immunohistochemistry for animal tissue Mice are injected with indicated amounts of the molecules (CSP alone, CSP-CTPB and/or CSP-COMPOUND 1) and after defined time-periods, they are deeply anesthetized with pentobarbital and perfused transcardially with 150 ml ice-cold paraformaldehyde (4% in 0.1M PB, 4° C.). Brains are then rapidly removed from the skull and post-fixed for about 6 hours in the same fixative at about +4° C. Fixed brains are then kept in sucrose at about +4° C. for about 48 hours. Freezing of the brains are then performed in isopentane for about 1 minute at about −40° C. and stored in −80° C. freezer. Coronal sections of about 20 µm in thickness are made through the dorsal hippocampus using the vibratome (Leica VT1000M). CSP, CSP-CTPB and/or CSP-COMPOUND 1 treated mice brain sections are kept in a same poly lysine coated slides. The tissue sections are permeabilized in 1XPBS/Triton 2% for about 15 mins. Non specific labeling is blocked by 1XPBS/Triton 0.1%/horse serum 5% for about 30 minutes at about 37° C. The slices are then incubated overnight with the indicated antibodies in appropriate dilutions and then washed, followed by incubation with secondary antibody conjugated with horseradish peroxidase in appropriate dilutions for about 1 hour. After three washes with 1XPBS/Triton 0.1%, the revelation is carried out with diaminobenzidine (DAB 0.05%, Tris 0.04M, pH 7.5, $H_2O_2$ 0.03%) and mounted.

Results

1. Chemically Conjugated COMPOUND 1 with CSP Efficiently Enter SHSY 5Y Cells and Induce HAT Activation To check the cell permeability of CSP-COMPOUND 1, SHSY 5Y neural cells are treated with 500 µM CSP, 500 µM CSP-COMPOUND 1 and Sodium Butyrate+Trichostatin A (TSA) (1 mM+2 µM respectively) for about 24 hours and histone acetylation is measured by immunofluorecence analysis using antibodies against acetylated H3K14. Immunofluorescence and the subsequent quantification of the intensity prove the activation of histone H3K14 acetylation by CSP-COMPOUND 1 composition (FIG. 8A).

SHSY 5Y cells are either treated with CSP or CSP-COMPOUND 1 and cells are harvested followed by the isolation of histones after 6 hours, 12 hours or 24 hours of treatment. Immunoblotting is performed using antibodies against acetylated H3K9 and H3K14. Enhancement of H3K14 acetylation is observed upon treatment of CSP-COMPOUND 1 (compare lanes 1, 2 and 3 versus lanes 4, 5 and 6) (FIG. 8B). Maximum amount of H3K14 acetylation is observed upon 12 hours of CSP-COMPOUND 1 treatment.

2. CSP-COMPOUND 1 Crosses the Blood Brain Barrier (BBB) and Enters Brain Cells In-Vivo To study the ability of CSP-COMPOUND 1 to cross the BBB, 250 µg of CSP-COMPOUND 1 composition is injected intraperitonially into mice and after 3 days, brain tissue is fixed with paraformaldehyde and further processed for confocal assays. Confocal laser microscopy at 560 nm confirms the presence of CSP-COMPOUND 1 in the brain (FIG. 9).

3. Time Dependent Localization of CSP-COMPOUND 1 in Mice Brain and Other Organs

To check the retention of CSP-COMPOUND 1 in mice brain, CSP-COMPOUND 1 is injected at five different time points i.e. 1 day, 3 days, 7 days, 14 days and 21 days respectively. The presence of CSP is confirmed in the cortex region of mice brain by confocal microscopy. After 24 hours of injection, CSP-COMPOUND 1 efficiently crosses the blood brain barrier (BBB) and gets localized in the mice brain but most of it is unable to enter the nucleus (FIG. 10A). At day 3, maximum number of CSP-COMPOUND 1 is found to be localized in the nucleus of brain cells. The presence of conjugated nanoparticles (i.e. CSP-COMPOUND 1) steadily decreases from day 7 onwards (FIGS. 10A, B). CSP localization is also checked after 24 hours of injection in other organs like liver, spleen, kidneys and lungs. Apart from brain, presence of CSP-COMPOUND 1 is detected in liver and spleen, whereas it is found to be completely absent in kidneys and lungs (FIG. 11). A time dependent study reveals that the presence of CSP-COMPOUND 1 steadily decreases in liver (FIG. 12A) and spleen (FIG. 12B) from day 3 onwards and almost no trace of it is observed on day 7 and onwards.

4. CSP-COMPOUND 1 Induces Hyperacetylation of Histone H2B and H3 in Mice Brain But Not in Liver Being a HAT activator, the effect of CSP-COMPOUND 1 is checked for its ability to induce acetylation of histones H3 and H2B in the cortex of the brain and in the liver after two different exposure times to CSP and CSP-COMPOUND 1 molecules. After 3 days of injection, it is observed that CSP-COMPOUND 1 conjugate induces both H3 and H2B acetylation in the brain (cortex), while no modification is seen in the liver (FIGS. 13A, B). Together, these studies (i.e. CSP-COMPOUND 1 localization studies and histone acetylation studies) also suggest that CSP-COMPOUND 1 has no major side effects outside of the brain.

5. CSP-COMPOUND 1 Induces Hyperacetylation of Histone H2B, H3 and H4K12 in the Hippocampus of Mice Brain The effect of CSP-COMPOUND 1 is further checked for its ability to induce histone acetylation in different brain regions and its involvement in long term memory and systemic consolidation (i.e. hippocampus and prefrontal cortex) upon 3 days of intraperitonial injection.

a) Enhancement of Histone H2B Acetylation

DAB (3',3'-diaminobenzidine tetrahydrochloride) staining on the anti acetylated H2B antibody treated tissue sections shows increased precipitation in CSP-COMPOUND 1 treated mice compared to CSP treated mice, suggesting hyperacetylation in the hippocampus (FIG. 14A). H2B acetylation of CA1, CA3 and dentate gyms are all induced and shows higher levels of acetylation on CSP-COMPOUND 1 treatment when compared to CSP treated mice tissues. The same experiment is repeated by staining with fluorescent labeled secondary antibodies (FIG. 14B). The dentate gyms region of hippocampus is extensively studied for levels of histone H2B acetylation. The IF results clearly shows the enhancement of H2B acetylation in the dentate gyms region of hippocampus of mice treated with CSP COMPOUND 1. To correlate with the results of immunohistochemical assays, the total nuclear proteins are isolated from the dorsal hippocampus and are subjected to immunoblotting (FIG. 14C). Histone H2B acetylation is found to be increased in CSP-COMPOUND 1 treated mice hippocampus (FIG. 14C, compare lanes 1 to 4 versus 5 to 8) wherein total histone H2B is taken as loading control. Quantification of the intensities of the bands proves that CSP-COMPOUND 1 induces histone H2B acetylation in hippocampus by around 2 fold (FIG. 14D).

b) Enhancement of Histone H3 and H4 Acetylation

The mice tissues are again processed for histone H4K12 and histone H3K14 acetylation. The immunohistological assays yield an enhancement of histone H3 acetylation in the hippocampus upon injection of CSP-COMPOUND 1. Despite high basal levels of H3K14 acetylation in the dentate gyrus, immunofluorescence assays also show an enhancement of H3K14 acetylation by CSP-COMPOUND 1 in this region (FIG. 15A). The tissue sections are also stained for H4K12 acetylation and an activation of acetylation is observed (FIG. 15B). To confirm these results, immunoblotting is performed using total nuclear protein from hippocampus wherein the said total nuclear protein is stained with antibody against acetylated H3 and H4K12 whereas actin antibody is taken as loading control (FIG. 16A). The quantification of the band intensity yield an enhancement of around 2-fold for H3 acetylation and 1.6-fold for H4K12 acetylation (FIG. 16B).

6. CSP-COMPOUND 1 Induces Hyperacetylation of Histone H2B, H3 and H4K12 in the Prefrontal Cortex of Mice Brain Activation of histone acetylation mediated by CSP-COMPOUND 1 is also checked in other brain parts. In particular, the prefrontal cortex of mice brain is isolated after 3 days of intraperitonial injection with CSP or CSP-COMPOUND 1 composition. The total nuclear proteins are isolated and are used for studying the activation of histone acetylation.

a) Enhancement of Histone H2B Acetylation

To study the effect of CSP-COMPOUND 1 conjugate in histone acetylation in prefrontal cortex, immunoblotting is performed with antibody against acetylated histone H2B and actin is used as loading control (FIG. 17A). CSP-COMPOUND 1 induces H2B acetylation in prefrontal cortex by about 2.4 fold in comparison to 1-fold increase by CSP alone (FIG. 17B).

b) Enhancement of Histone H3 Acetylation

Alteration of histone H3 acetylation upon treatment of CSP or CSP-COMPOUND 1 is also studied in prefrontal cortex COMPOUND 1 (FIG. 17C). Immunoblotting studies reveal around 2.2 fold induction of histone H3 acetylation in prefrontal cortex by CSP-COMPOUND 1 in comparison to 1-fold increase by CSP alone (FIG. 17D).

7. CSP-COMPOUND 1 Induces Neurogenesis in the Subgranular Zone (SGZ) of the Dentate Gyrus of Hippocampus and the Subventricular Zone (SVZ) of the Lateral Ventricles in Mice Brain CSP-COMPOUND 1 induces hyper acetylation of histone H2B in the dentate gyrus. This region is one of the two regions of the brain where adult neurogenesis occurs. New neurons generate from the neural stem cells present in the inner regions of the dentate gyrus. Double cortin is a protein which is expressed in the first two weeks of neural development and is used as a marker for neurogenesis. Immunofluorescence of the tissue section containing the hippocampus is performed using antibody against double cortin. The results show that the mice treated with COMPOUND 1 doesn't show double cortin expression which establishes the ineffectiveness of COMPOUND 1 on neurogenesis (FIG. 18). Surprisingly, mice treated with CSP-COMPOUND 1 show increased number of neurons expressing double cortin (FIG. 18). This result is also verified by immunohistochemical assays using double cortin and staining with DAB (FIG. 19). In consistent with the IF report, CSP-COMPOUND 1 treated mice show more number of neurons expressing double cortin. One interesting finding is that the length of the neuronal axons and the dentritic branching of the neurons expressing double cortin is increased in CSP-COMPOUND 1 treated mice in comparison with CSP treated mice, establishing a role of CSP-COMPOUND 1 in neural survival, differentiation and integration in the brain circuitry (FIG. 19).

To further evaluate whether CSP-COMPOUND 1 has a specific effect on the hippocampal niche of adult neurogenesis or if it can act more generally throughout the brain, studies are carried out for doublecortin expression in response to CSP-COMPOUND 1 in the subventricular zone (SVZ) of the lateral ventricles region, which is the second niche of adult neurogenesis. Immunohistochemical assays with antibody against doublecortin show increased expression of newly generated neurons on the walls of SVZ in CSP-COMPOUND 1 treated mice when compared to CSP treated mice (FIGS. 20 A and B).

Example 6

Spatial Memory Testing in the Morris Water Maze (MWZ)

Ten mice in each group (CSP or CSP-COMPOUND 1 injected), are used for acquisition with a hidden platform for starting randomly from each of the four cardinal points from the edge of the pool for 3 consecutive days to learn the location of the platform hidden 1 cm below the water surface in the south west quadrant. The distance travelled is recorded by a video tracking system (Ethovision, Noldus, the Netherlands). At the end of acquisition, all mice trained with hidden platform are tested for retention in a probe trial administered 48 hours and 14 days after the last acquisition trial. The platform is removed and each mouse is released from the north-east start point and given 60 seconds to swim. The variable taken into account for the probe trial is the time spent in each of the four quadrants.

Results

CSP-COMPOUND 1 Improves Long Term Memory Formation

Fine tuning of transcriptional regulation is required for memory formation and increasing evidences in the art demonstrate the participation of acetyltransferase activity, and particularly that of CBP, in these processes. Increased histone acetylation has been associated with improvement of diverse forms of memory. Treatment of mice with CSP-COMPOUND 1 is tested for its potential promnesic effect in reference memory, the task being to find the spatial localization of a hidden platform in the Morris Water maze. A panel of different protocols have been performed, which establishes that CSP-COMPOUND 1 improves spatial memory retention in the long term. CSP-COMPOUND 1 does not have an impact on acquisition performance itself in the MWM (FIGS. 21A, 23A,B). While retention performances after spatial training are equal in CSP-COMPOUND 1 treated and CSP control mice as tested in a probe trial performed 1 day (FIG. 21B) or 2 days (FIG. 23A) after acquisition, the memory trace formed in trained CSP-COMPOUND 1 treated mice is more resistant to extinction than in CSP control mice (FIGS. 21C, D). Upon a weak learning (3-day acquisition), mice retention of the platform location is lost after 14 days (FIG. 22C). Interestingly, CSP-COMPOUND 1 still displays significant retention of the platform location when tested 16 days after a short training (FIG. 23B). Moreover, in the groups of mice that had been previously trained for 3 days and tested after 2 days, CSP-COMPOUND 1 mice still show a search in the correct quadrant when compared to CSP-treated mice (TQ compared to Other Q, FIG. 24A), indicating the persistence of the memory trace induced by the CSP-COMPOUND 1 conjugate. The mice injected with CSP-TTK21 are therefore good in spatial memory in comparison to CSP injected mice even at day 14 and day 16 probe tests. Remote spatial memory is documented to rely on the integration of new neuronal progenitors in the neuronal network and thus it is shown that here that CSP-COMPOUND 1 significantly improves consolidation by such mechanisms.

Example 7

Comparison of Activation of Histone Acetylation by CSP, CSP-CTPB and CSP-COMPOUND 1 Individually in Hippocampus of Mice Brain Comparison of Activation of Histone H2B Acetylation in Hippocampus of Mice Brain:

Similar experiments are performed as described in the above examples for comparing the histone H2B acetylation activity of CSP, CSP-CTPB and CSP-COMPOUND 1 when given individually. In particular, mice are injected with either CSP alone, CSP-CTPB or CSP-COMPOUND 1 (20 mg/kg each) followed by euthanization of mice 3 days later.

Immunofluorescent labeling of mouse dorsal hippocampus using antibodies against tetra-acetylated H2B showcases significant increase in H2B acetylation in CSP-COMPOUND 1 treated mice when compared to CSP alone or CSP-CTPB treated mice (FIG. 25).

The aforementioned results pertaining to histone H2B acetylation is further confirmed by western blot analysis. In particular, three days post-injection of either CSP alone, CSP-CTPB or CSP-COMPOUND 1 (20 mg/kg of body weight), dorsal hippocampi are dissected out and total protein extracts are analysed by western blots with antibodies against tetra-acetylated H2B histone (FIG. 26 A). FIG. 26 B further depicts the quantification of acetylated histone H2B which is shown relative to the total amount of the H2B.

Comparison of activation of histone H3 acetylation in hippocampus of mice brain: Similar experiments are performed as described in the above examples for comparing the histone H3 acetylation activity of CSP, CSP-CTPB and CSP-COMPOUND 1 when given individually. Mice are injected with either CSP alone, CSP-CTPB or CSP-COMPOUND 1 (20 mg/kg each) followed by euthanization of mice 3 days post injection. Immunohistochemistry is performed on 20 μm-thick cryosections with an anti-acetylated H3 Lys 14 antibody. H3 acetylation is observed to be significantly increased in all hippocampal areas in CSP-COMPOUND 1 treated mice when compared to CSP alone or CSP-CTPB treated mice (FIG. 27 A). Further, immunofluorescent labeling and western blot of mouse dorsal hippocampus using antibodies against acetylated H3 Lys 14 showcase significant increase in H3 acetylation in CSP-COMPOUND 1 treated mice when compared to CSP alone or CSP-CTPB treated mice (FIGS. 27 B, C and D).

Example 8

Comparison of Long Term Memory Enhancement Between CSP, CSP-CTPB and CSP-COMPOUND 1

Similar Morris Water maze experiments are performed as described in previous examples with CSP, CSP-CTPB or CSP-COMPOUND 1 treated mice. Specifically, 10 mice per group are trained for three days and after 16 days, probe test is performed to identify any retention of spatial memory in the mice.

It is observed that mice injected with CSP-COMPOUND 1 spent more time in the target quadrant than the mice injected with CSP or CSP-CTPB, establishing that the mice injected with CSP-COMPOUND 1 could still remember the location of the platform which was used at the time of the acquisition. Thus, CSP-COMPOUND 1 conjugate efficiently and significantly enhances long term spatial memory whereas CSP-CTPB conjugate fails to enhance memory formation.

In an embodiment of the present disclosure, the CSP-COMPOUND 1 forms a stable conjugate due to the ability of formation of covalent bonds. Said covalent conjugation provides for one of the several advantages to the CSP-COMPOUND 1 in terms of the amount/number of molecules of COMPOUND 1 required for conjugation. This is in sharp contrast to the prior art conjugates such as CSP-CTPB wherein, the CTPB is conjugated to CSP via. adsorption. Said adsorption of CTPB with CSP requires large amount of CTPB molecules and also, the conjugation is not very stable. Additionally, the CTPB in CSP-CTPB conjugate easily gets dissociated while being transferred through the blood brain barrier and hence the final amount of CTPB reaching the brain is not at all definite. Thus, from a therapeutic perspective, it would be much more beneficial to employ the CSP-COMPOUND 1 of the instant invention to ensure the stability and amount of compound being administered to a subject in need. Hence, the present disclosure overcomes the drawbacks of the conjugates known in the prior art by providing for CSP-COMPOUND 1 conjugate which is highly stable and requires less amount/concentration of COMPOUND 1 to induce histone acetylation in organs such as brain, liver and spleen.

Based on the above description along with the accompanying examples and figures, it is concluded that the carbon nanosphere-HAT activator composition (i.e. CSP-COMPOUND 1 composition) of the present disclosure has various advantages such as:

covalent conjugation of COMPOUND 1 and the carbon nanosphere;
ability of the CSP-COMPOUND 1 conjugate to induce histone acetylation in organs such as brain, liver and spleen;
the specific ability of the CSP-COMPOUND 1 conjugate to cross blood brain barrier (BBB) and induce histone acetylation in brain;
ability of CSP-COMPOUND 1 conjugate to enhance neurogenesis and long-term memory formation;
improved efficiency in terms of histone acetylation, neurogenesis and long-term memory as mentioned above when compared to CSP alone and other nanosphere-HAT activator compositions such as CSP-CTPB.

Aforesaid advantages of said composition of the present disclosure thus provides for managing number of disorders in a subject, such as aging-related, neurodegenerative diseases (Alzheimer's in particular), neurological disorders, depression or other kinds of disorders in which increased HAT activity, neurogenesis and/or memory improvement would benefit.

We claim:

1. A composition comprising nanosphere and histone acetyltransferase (HAT) activator, wherein the HAT activator is N-(4-Chloro-3-trifluoromethyl-phenyl)-2-n-propoxy-benzamide.

2. The composition as claimed in claim 1, wherein the nanosphere is an intrinsically fluorescent carbon nanosphere (CSP); and wherein the N-(4-Chloro-3-trifluoromethyl-phenyl)-2-n-propoxy-benzamide is covalently conjugated with said carbon nanosphere.

3. A process for obtaining a composition comprising nanosphere and histone acetyltransferase (HAT) activator, wherein the HAT activator is N-(4-Chloro-3-trifluoromethyl-phenyl)-2-n-propoxy-benzamide, said process comprising conjugating the N-(4-Chloro-3-trifluoromethyl-phenyl)-2-n-propoxy-benzamide with the nanosphere to obtain said composition.

4. The process as claimed in claim 3, wherein the nanosphere is an intrinsically fluorescent carbon nanosphere (CSP).

5. The process as claimed in claim 3, wherein the N-(4-Chloro-3-trifluoromethyl-phenyl)-2-n-propoxy-benzamide is obtained by a process comprising steps of:
    reacting salicyclic acid (A) with iodopropane (B) in presence of acetone and potassium carbonate to obtain propyl 2-propoxy-benzoate (C);
    reacting the propyl 2-propoxy-benzoate with potassium tertiary butoxide in presence of dimethyl sulfoxide to obtain 2-propoxy-benzoic acid (D);
    reacting the 2-propoxy-benzoic acid with thionyl chloride in presence of dimethylformamide and dichloromethane to obtain 2-propoxy-benzoyl chloride (E); and
    converting the 2-propoxy-benzoyl chloride in presence of 5-amino-2-chloro benzotriflouride to obtain the N-(4-Chloro-3-trifluoromethyl-phenyl)-2-n-propoxy-benzamide.

6. The process as claimed in claim 3, wherein the conjugation is covalent conjugation; and wherein, the conjugation comprises steps of:
    adding N-(4-Chloro-3-trifluoromethyl-phenyl)-2-n-propoxy-benzamide to a solution containing nanosphere in presence of thionyl chloride, dimethylformamide and dichloromethane to obtain a reaction mixture; and
    stirring the reaction mixture at a temperature ranging from about 28° C. to about 30° C., for a time-period ranging from about 8 hours to about 9 hours to obtain the composition.

7. The process as claimed in claim 6, wherein the process further comprises evaporation, washing and centrifugation; and wherein the composition is dried at a temperature ranging from about 50° C. to about 70° C., for a time-period ranging from about 2 days to about 3 days.

8. A method of inducing acetylation of histone by histone acetyltransferase (HAT), said method comprising act of contacting said histone acetyltransferase (HAT) with a composition comprising nanosphere and histone acetyltransferase (HAT) activator wherein the HAT activator is N-(4-Chloro-3-trifluoromethyl-phenyl)-2-n-propoxy-benzamide, for inducing the acetylation of histone.

9. The method as claimed in claim 8, wherein the composition induces histone acetylation in organs selected from group comprising brain, liver and spleen or any combination thereof.

10. The method as claimed in claim 9, wherein the composition induces histone acetylation in the brain by crossing blood brain barrier and entering nucleus of brain cells.

11. The method as claimed in claim 8, wherein said method is employed for inducing neurogenesis or enhancing long-term memory formation or a combination thereof.

12. The method as claimed in claim 8, wherein the histone is selected from a group comprising H2B, H3 and H4 or any combination thereof.

13. The method as claimed in claim 8, wherein the histone acetyltransferase (HAT) is selected from a group comprising p300/CBP and PCAF (p300/CBP Associated factor) or a combination thereof.

14. The method as claimed in claim 8, wherein the nanosphere is an intrinsically fluorescent carbon nanosphere (CSP).

\* \* \* \* \*